(12) United States Patent
Wilsey et al.

(10) Patent No.: US 8,008,037 B2
(45) Date of Patent: Aug. 30, 2011

(54) MATRIX COMPOSITION WITH ALKYLPHENAZINE QUATERNARY SALT AND A NITROSOANILINE

(75) Inventors: Christopher D. Wilsey, Carmel, IN (US); Mitali Ghoshal, Noblesville, IN (US); Herbert Wieder, Manheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 153 days.

(21) Appl. No.: 12/056,473

(22) Filed: Mar. 27, 2008

(65) Prior Publication Data

US 2009/0246808 A1 Oct. 1, 2009

(51) Int. Cl.
*C12Q 1/32* (2006.01)
(52) U.S. Cl. ............................. 435/26; 544/35; 544/332
(58) Field of Classification Search .................... 435/14, 435/26; 544/35, 332
See application file for complete search history.

(56) References Cited

U.S. PATENT DOCUMENTS

| | | |
|---|---|---|
| 4,490,464 A | 12/1984 | Gorton et al. |
| 5,122,244 A | 6/1992 | Hoenes |
| 5,206,147 A | 4/1993 | Hoenes |
| 5,278,047 A | 1/1994 | Lilja et al. |
| 5,286,362 A | 2/1994 | Hoenes et al. |
| 5,393,615 A | 2/1995 | Corey et al. |
| 5,498,542 A | 3/1996 | Corey et al. |
| 5,520,786 A | 5/1996 | Blockzynski et al. |
| 5,571,395 A | 11/1996 | Park et al. |
| 5,707,820 A | 1/1998 | Wilsey et al. |
| 5,783,056 A | 7/1998 | Hampp et al. |
| 5,858,691 A | 1/1999 | Hoenes et al. |
| 5,866,353 A | 2/1999 | Berneth et al. |
| 5,902,731 A | 5/1999 | Ouyang et al. |
| 6,057,120 A | 5/2000 | Heindl et al. |
| 6,120,676 A | 9/2000 | Heller et al. |
| 6,200,773 B1 | 3/2001 | Ouyang et al. |
| 6,270,637 B1 | 8/2001 | Crismore et al. |
| 6,352,824 B1 | 3/2002 | Buck, Jr. et al. |
| 6,475,372 B1 | 11/2002 | Ohara et al. |
| 6,720,164 B1 | 4/2004 | Shinozuka et al. |
| 6,736,957 B1 | 5/2004 | Forrow et al. |
| 6,852,502 B1* | 2/2005 | Martin ........................... 435/25 |
| 6,939,685 B2 | 9/2005 | Ouyang et al. |
| 2003/0116447 A1 | 6/2003 | Surridge et al. |
| 2004/0238359 A1* | 12/2004 | Ikeda et al. ................ 204/403.1 |
| 2005/0164329 A1 | 7/2005 | Wallace-Davis et al. |
| 2006/0003400 A1 | 1/2006 | Byrd et al. |
| 2008/0090278 A1* | 4/2008 | Kitabayashi et al. ......... 435/188 |
| 2009/0246808 A1* | 10/2009 | Wilsey et al. ................... 435/14 |

FOREIGN PATENT DOCUMENTS

| | | |
|---|---|---|
| EP | 0 285 998 | 10/1988 |
| EP | 2000/606296 B1 | 3/1999 |
| EP | 2000/654079 B1 | 3/2000 |
| EP | 2000/704535 B1 | 11/2001 |
| EP | 2000/986748 B1 | 9/2006 |
| WO | WO 98/55856 | 10/1998 |
| WO | WO 99/19507 A1 | 4/1999 |

OTHER PUBLICATIONS

Yomo T. et al. Preparation and Kinetic Properties of 5-Ethylphenazine Glucose Dehydrogenase NAD+ Conjugate . . . European J of Biochemistry 200(3)759-766, 1991.*

Maeda Masaka et al., "Flow injection determination of glucose, bile acid and ATP using immobilized enzyme reaactor and chemiluminescent assay of NAD(P)H" Journal of Bioluminesence and Cehmiluminescence, vol. 8, No. 5, 1993, pp. 241-246 XP9119741 ISSN: 0884-3996.

Yomo et al., "Preparation and kinetic properties of 5-ethylphenazine-glucose-dehydrogenase-NAD+ conjugate, a semisynthetic glucose oxidase" European Journal of Biochemistry 1991 DE, vol. 200, No. 3, 1991, pp. 759-766 XP1121999, Blackwell Publishing, Berlin, DE, ISSN 0014-2956.

Yomo, et. al. Synthesis & Characterization of a 1-substituted 5-alkylphenazine derivatives carrying functional groups European Journal of Biochemistry. 179, 293-298 (1989).

* cited by examiner

*Primary Examiner* — Ralph Gitomer
(74) *Attorney, Agent, or Firm* — Woodard, Emhardt, Moriarty, McNett & Henry LLP

(57) ABSTRACT

A chemistry matrix for use in determining the concentration of an analyte in a biological fluid includes a glucose dehydrogenase, nicotinamide adenine dinucleotide, an alkylphenazine quaternary salt, and/or a nitrosoaniline. The chemistry matrix is used with an electrochemical biosensor to determine the concentration of an analyte after a reaction occurs within the biosensor, at which time an analysis is completed to determine the concentration. A method of determining the concentration of an analyte using the chemistry matrix of glucose dehydrogenase, nicotinamide adenine dinucleotide, an alkylphenazine quaternary salt, and/or a nitrosoaniline is another aspect that is described. The method also further features test times of five seconds or less. Methods utilizing the new chemistry matrix can readily determine an analyte such as blood glucose at concentrations of from about 20-600 mg/dL at a pH of from about 6.5 to about 8.5.

22 Claims, 5 Drawing Sheets

MATRIX COMPOSITION WITH ALKYLPHENAZINE QUATERNARY SALT AND A NITROSOANILINE

BACKGROUND

1. Technical Field

The present disclosure generally relates to a chemistry matrix and methods for measuring the presence and/or concentration of an analyte in a biological fluid. More specifically, but not exclusively, the present disclosure relates to a chemistry matrix and methods that increase the analyte specificity when measuring analyte with an electrochemical biosensor in the presence of interfering substances. As used herein, the term "chemistry matrix" refers to a physical region containing at least one chemical substance capable of reacting with an analyte.

2. Description of Related Art

Measuring the concentration of substances, particularly in the presence of other confounding substances and under varied conditions, is important in many fields. For example, the measurement of glucose in bodily fluids, such as blood, under varied conditions and in the presence of interfering substances, is crucial to the effective treatment of diabetes. The failure to properly control blood glucose levels can produce extreme complications, including blindness and loss of circulation in the extremities, which can ultimately deprive the diabetic of use of his or her fingers, hands, feet, etc.

Test strips are often used to measure the presence and/or concentration of selected analytes in test samples. For example, a variety of test strips are used to measure glucose concentrations in blood to monitor the blood sugar level of people with diabetes. These test strips include a reaction chamber into which a reagent composition has been deposited. Current trends in test strips require smaller test samples and faster test analysis times. A significant benefit is provided to the patient when using smaller test samples, which can be obtained from less sensitive areas of the body, such as the forearm. Additionally, faster and more accurate test times provide added convenience and better control of the patient's blood sugar level.

Several methods are known for measuring the concentration of analytes, such as, for example, glucose, in a blood sample. Such methods typically fall into one of two categories: optical methods and electrochemical methods. Optical methods generally involve reflectance or absorbance spectroscopy to observe the spectrum shift in a reagent. Such shifts are caused by a chemical reaction that produces a color change indicative of the concentration of the analyte. Electrochemical methods generally involve amperometric, coulometric, potentiometric, and/or conductive responses indicative of the concentration of the analyte. See, for example, U.S. Pat. No. 4,233,029 to Columbus; U.S. Pat. No. 4,225,410 to Pace; U.S. Pat. No. 4,323,536 to Columbus; U.S. Pat. No. 4,008,448 to Muggli; U.S. Pat. No. 4,654,197 to Lilja et al.; U.S. Pat. No. 5,108,564 to Szuminsky et al.; U.S. Pat. No. 5,120,420 to Nankai et al.; U.S. Pat. No. 5,128,015 to Szuminsky et al.; U.S. Pat. No. 5,243,516 to White; U.S. Pat. No. 5,437,999 to Diebold et al.; U.S. Pat. No. 5,288,636 to Pollmann et al.; U.S. Pat. No. 5,628,890 to Carter et al.; U.S. Pat. No. 5,682,884 to Hill et al.; U.S. Pat. No. 5,727,548 to Hill et al.; U.S. Pat. No. 5,997,817 to Crismore et al.; U.S. Pat. No. 6,004,441 to Fujiwara et al.; U.S. Pat. No. 4,919,770 to Priedel et al.; and U.S. Pat. No. 6,054,039 to Shieh, which are hereby incorporated by reference in their entireties. Electrochemical methods typically use blood glucose meters (but not always) to measure the electrochemical response of a blood sample in the presence of a reagent. The reagent reacts with the glucose to produce charge carriers that are not otherwise present in blood. Consequently, the electrochemical response of the blood in the presence of a given signal is intended to be primarily dependent upon the concentration of blood glucose. Typical reagents used in electrochemical blood glucose meters are disclosed in U.S. Pat. Nos. 5,997,817, 5,122,244, and 5,286,362, which are hereby incorporated by reference in their entireties.

A number of error sources can create inaccurate results when measuring analyte levels in body fluid. Sometimes harsh conditions to which the sensor is exposed worsen the accuracy of the sensor. Occasionally, the sensor can experience harmful conditions, often termed "strip rotting" or "vial abuse", which refers to when the sensors during storage are abused and exposed to detrimental conditions, such as excessive heat, light, and/or moisture. This exposure to excessive heat and/or moisture can result in slowing of the reaction times due to loss of enzyme activity.

In the past, these issues have been avoided by using enzymes that have very fast reaction times and high specific activities with the analyte being measured. By utilizing enzymes with these particular characteristics, reactions having high and similar levels of completion under all test conditions, such as at various temperatures and hematocrit levels, can be achieved. However, as a practical matter, enzymes usually cannot be incorporated with high enough amounts into the sensor without causing a significant loss in performance of the sensor. In addition, enzymes of high specific activities are not always desirable for all analytes. For example, such systems for determining glucose levels still fail to address the need of being free from the effects of interferents, such as maltose, galactose, xylose, and the like, which can create inaccurate readings.

For example, patients undergoing peritoneal dialysis or IGG therapy can experience high levels of maltose in their blood, which can interfere with accurate blood glucose readings. Therefore, interference from maltose can be a significant problem. As an illustration, Abbott Laboratories' Freeystyle® blood glucose monitoring system employs a glucose-dye-oxidoreductase (GlucDOR) enzyme in conjunction with a coulometric technique with a variable test time. However, such a system is still clinically unacceptable due to interference from maltose, and, as a practical matter, the use of coulometry, as currently practiced, has a number of significant drawbacks. Further, attempts have been made to minimize the maltose interference effect by cloning new GlucDOR enzymes with a greater specificity to glucose. However, progress has not resulted in a feasible solution.

In still yet another example, Abbott Laboratories' PCx/ TrueMeasure™ system utilizes amperometry coupled with a Nicotinamide Adenine Dinucleotide (NAD)-dependent Glucose Dehydrogenase enzyme (GDH/NAD) to provide a system substantially free from maltose interference. However, the amperometric system can provide inaccurate readings because of blood oxygen level (pO2) interference, an effect that causes readings of glucose levels to vary due to a variety of factors including where the sample is taken. For example, blood oxygen levels can vary substantially depending on whether the sample is capillary, venous, or arterial blood. Consequently, to minimize oxygen interference, a user of this system must indicate the source or nature of the blood sample prior to sampling. As can be appreciated, requiring the user to enter information regarding the blood sample provides an additional source of error if the information is erroneously entered by the user.

In addition to slowing enzyme activity, vial abuse can also result in an increase of background current, sometimes referred to as "blank current", when readings are taken. A variety of sources for background or blank current exist. For instance, it is desirable that mediators, which are used to transfer electrons from the enzyme to the electrode, be in an oxidized state before the sensor is used. Over time the heat and/or humidity from the vial abuse will tend to reduce the mediator. If part of the mediator is in a reduced form before the sensor is used, a portion of the current will result from the working electrode oxidizing the reduced form of the mediator. The resulting background or blank current will tend to bias the mediator, which in turn can lead to inaccurate results. Other impurities in the reagent can also increase background or blank current problems.

Amperometric sensors have been proposed that use a "burn-off" approach to address the blank current problem. In this approach, two DC signals are applied to the sensor. The first DC signal, or burn-off signal, is used to consume or oxidize any species responsible for the blank current in the same diffusion layer that is later used to analyze the analyte. Afterwards, the second signal, or analysis signal, is used to analyze the analyte levels. Both the burn-off and analysis potentials have the same polarity. Although this burn-off technique reduces the effect of blank or background current, it does so at the expense of partially oxidizing (or reducing) the analyte to be measured, thereby reducing the noise-to-signal ratio of the sensor. Moreover, such techniques have failed to compensate for variations in reaction time caused by factors like temperature and enzymes with slow/variable reaction velocities, to name a few examples. In addition, the enzymes used in such sensors tend to be susceptible to maltose interference.

In view of the above, it is desirable for a biosensor utilized to measure an analyte (such as glucose) to have a chemistry matrix with increased specificity for the analyte, and to be capable of minimizing interferences resulting from fluctuations in oxygen levels and from interfering substances such as maltose. It is further desirable to provide a chemistry matrix that is photochemically stable.

BRIEF SUMMARY

Embodiments of the compositions, methods and devices disclosed herein involve a chemistry matrix having increased specificity for an analyte (such as glucose) that is capable of minimizing interferences resulting from fluctuations in oxygen levels and from related substances (such as maltose). Broadly, the chemistry matrix comprises glucose dehydrogenase, nicotinamide adenine dinucleotide, a phenazine derivative and a nitrosoaniline. Preferred embodiments of the chemistry matrix are typically stable at a pH of from about 6.5 to about 8.5 and are photochemically stable. A chemistry matrix or components thereof are considered photochemically stable if the matrix or a component thereof remains colorless upon exposure to ordinary fluorescent lighting for at least one hour.

A first aspect of the present disclosure provides for a chemistry matrix composition for use in analyzing the concentration of an analyte. This chemistry matrix which is stable at a pH of from about 6.5 to about 8.5, is photochemically stable, and includes glucose dehydrogenase, nicotinamide adenine dinucleotide, an alkylphenazine quaternary salt, and a nitrosoaniline.

Suitable alkylphenazine quaternary salts useful in the present disclosure include, but are not limited to, 5-alkyl phenazines illustrated by formula Ia:

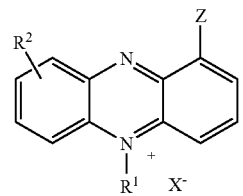

where:

Z is selected from the group consisting of —$(CH_2)_m$COOH, —NHAc, and —OY, where m is an integer ranging from 0 to about 6 and Y is selected from the group consisting of

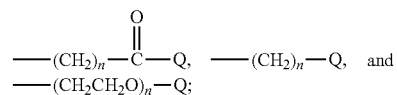

where n is an integer ranging from about 1 to about 4, Q is —OH, —$OR^1$, —$NH_2$, —$NHR^2$, —$NR^2R^3$, —$NH(CH_2)_o$$NR^2R^3$, —$NH(CH_2)_oOH$, —$NHCH_2CH_2$—(O $CH_2CH_2)_o$-G, —$(CH_2)_oNR^2R^3$, —$OCH_2CH_2)_oNR^2R^3$ and —$(OCH_2CH_2)_oOH$, where G is —COOH, $NR^2R^3$, or

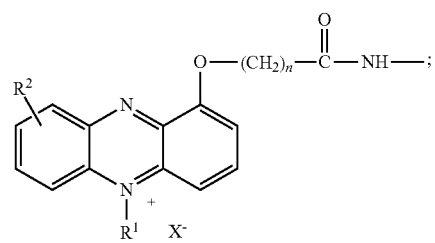

$R^1$ is a $C_1$ to $C_6$ alkyl group, $R^2$ and $R^3$ are the same or different and each represents a H or a $C_1$ to $C_6$ alkyl group, o is an integer ranging from about 1 to about 6; and X is an anion selected from the group consisting of halide, sulfate, alkyl sulfate, phosphate, phosphite, carboxylate, $CF_3COO^-$, $CH_3OSO_2^-$, $C_2H_5OSO_2^-$, and $CH_3SO_3^-$.

A second aspect of the present disclosure provides for a chemistry matrix composition that can be used to determine the concentration of an analyte where the chemistry matrix includes glucose dehydrogenase, nicotinamide adenine dinucleotide, a nitrosoaniline and a photochemically stable 5-alkyl-1-carboxyalkoxyphenazine useful for determining the concentration of an analyte. The "carboxy group" in a carboxyalkoxyphenazine group includes carboxylic acids, their salts, esters, amides, nitriles, and other known derivatives of carboxylic acids. Particularly suitable 5-alkyl-1-carboxyalkoxyphenazines are represented by the formula IIa below.

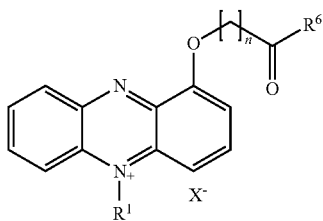

where $R^6$ is selected from the group consisting of —OH, —OR$^1$, —NH$_2$, —NHR$^2$, —NR$^2$R$^3$, —NH(CH$_2$)$_m$NR$_2$, —NH(CH$_2$)$_m$OH, —O(CH$_2$)$_m$NH$_2$, and —O(CH$_2$)$_m$OH, R$^1$ is a C$_1$ to C$_6$ alkyl group, R$^2$ and R$^3$ are the same or different and each represents a H or a C$_1$ to C$_6$ alkyl group, X$^-$ is an anion selected from the group consisting of halide, sulfate, alkyl sulfate, phosphate, phosphite, carboxylate, CF$_3$COO$^-$, CH$_3$OSO$_2^-$, C$_2$H$_5$OSO$_2^-$, and CH$_3$SO$_3^-$, and n and m are integers ranging from about 1 to about 6.

A third aspect of the present disclosure provides for a further chemistry matrix composition for use in analyzing the concentration of an analyte. This chemistry matrix includes:

(a) glucose dehydrogenase;
(b) nicotinamide adenine dinucleotide;
(c) a phenazine ethosulfate having the formula:

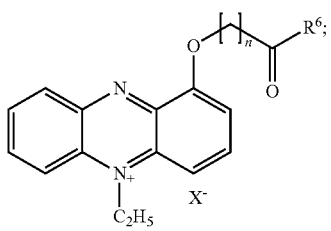

where $R^6$ is selected from the group consisting of —OH, —OR$^1$, —NH$_2$, —NR$^2$R$^3$, —NH(CH$_2$)$_m$NH$_2$, —NH(CH$_2$)$_m$OH, —O(CH$_2$)$_m$NH$_2$, and —O(CH$_2$)$_m$OH, R$^2$ and R$^3$ are the same or different and each represents a H or a C$_1$ to C$_6$ alkyl group, X$^-$ is an anion selected from the group consisting of halide, sulfate, alkyl sulfate, phosphate, phosphite, carboxylate, CF$_3$COO$^-$, CH$_3$OSO$_2^-$, C$_2$H$_5$OSO$_2^-$, and CH$_3$SO$_3^-$, n is an integer ranging from about 1 to about 6, m is an integer ranging from about 1 to about 6; and (d) a nitrosoaniline derivative having the formula:

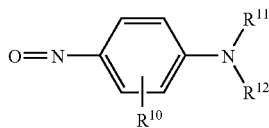

($R^{10}$ = 3-OCH$_3$, $R^{11}$ and $R^{12}$ = CH$_2$CH$_2$OH)

In this chemistry matrix, a phenazine of formula Ia can also be substituted for the phenazine of formula II above.

A forth aspect of the present disclosure provides for a chemistry matrix composition useful for determining the concentration of an analyte. The composition includes glucose dehydrogenase, nicotinamide adenine dinucleotide, a nitrosoaniline and a photochemically stable 1-carboxyalkyloxy-5-alkylphenazine.

A fifth aspect of the present disclosure provides for a method for the electrochemical analysis of an analyte in a liquid sample that involves reacting the analyte with the matrix which includes glucose dehydrogenase, nicotinamide adenine dinucleotide, a nitrosoaniline and a photochemically stable 1-carboxyalkyloxy-5-alkylphenazine to provide an electro-active agent capable of producing an electrochemical response, providing a signal to produce an electrochemical response, measuring the electrochemical response produced, and determining the analyte concentration in the liquid sample based on the electrochemical response measured. This method typically involves applying the sample to an application area of a biosensor having a test strip therein including an embodiment of the chemistry matrix described above, and quantifying the analyte by reaction with the chemistry matrix. The method is particularly effective in determining blood glucose levels ranging from about 20 mg/dL to about 600 mg/dL and can provide test times of about 5 seconds or less. Test time refers to the time between applying a test sample to a test strip (or actually detecting the applying of the test sample) and when a test result is obtained and displayed on the display of a monitoring device configured for use with the biosensor.

A sixth aspect of the present disclosure provides a method for the electrochemical analysis of an analyte in a liquid sample, which comprises applying the sample to an application area of a biosensor having a test strip including the chemistry matrix, quantifying the analyte by reaction with the chemistry matrix and displaying a result of said quantifying on a display of a monitoring device configured for use with said biosensor, wherein said chemistry matrix includes glucose dehydrogenase, nicotinamide adenine dinucleotide, a nitrosoaniline, and a 5-alkylphenazine quaternary salt having the formula:

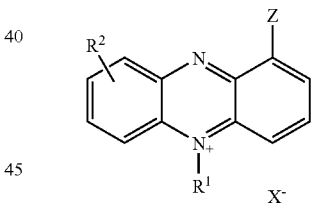

where:

Z is selected from the group consisting of —(CH$_2$)$_m$COOH, —NHAc, and —OY, where m can any integer ranging from 0 to about 6 and Y is selected from the group consisting of

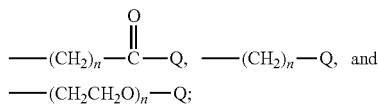

where n is an integer ranging from about 1 to about 4, Q is —OH, —OR$^1$, —NH$_2$, —NHR$^2$, —NR$^2$R$^3$, —NH(CH$_2$)$_o$NR$^2$R$^3$, —NH(CH$_2$)$_o$OH, —NHCH$_2$CH$_2$—(OCH$_2$CH$_2$)$_o$-G, —(CH$_2$)$_o$NR$^2$R$^3$, —OCH$_2$CH$_2$)$_o$NR$^2$R$^3$ and —(OCH$_2$CH$_2$)$_o$OH, where G is —COOH, NR$^2$R$^3$, or

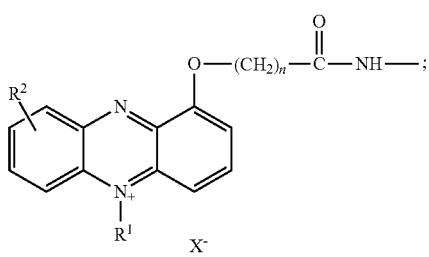

$R^1$ is a $C_1$ to $C_6$ alkyl group, $R^2$ and $R^3$ are the same or different and each represents a H or a $C_1$ to $C_6$ alkyl group, o is an integer ranging from about 1 to about 6; and X is an anion selected from the group consisting of halide, sulfate, alkyl sulfate, phosphate, phosphite, carboxylate, $CF_3COO^-$, $CH_3OSO_2^-$, $C_2H_5OSO_2^-$, and $CH_3SO_3^-$. Although a variety of nitrosoanilines can be utilized in the chemistry matrix for this method, the nitrosoaniline illustrated by structure III is particularly suitable.

Numerous advantages and additional aspects of the present disclosure will be apparent from the description of the preferred embodiments and drawings that follow.

DETAILED DESCRIPTION

Figure 1:
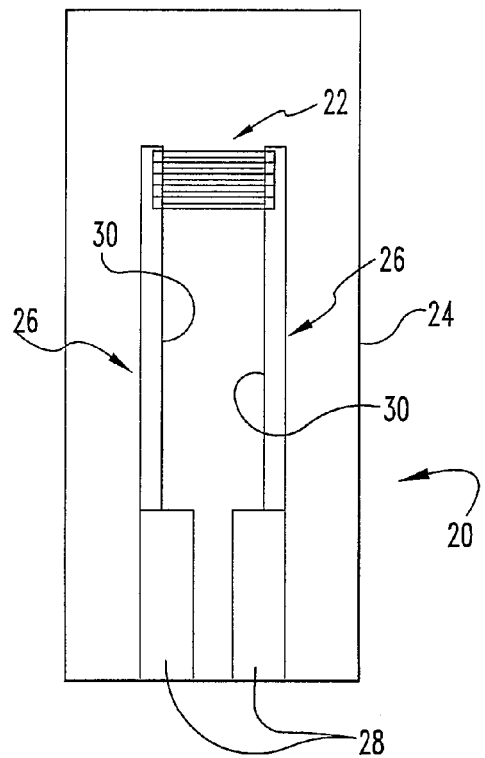
FIG. 1 is a first top view of a test strip used with embodiments of the present disclosure and includes a cover layer of the test strip removed.

For the purpose of promoting an understanding of the principles of the disclosure, reference will now be made to the embodiments illustrated in the drawings and specific language will be used to describe the same. It will nevertheless be understood that no limitation of the scope of the disclosure is thereby intended. Such alterations and further modifications in the illustrated device and such further applications of the principles of the disclosure as illustrated therein as would normally occur to one skilled in the art to which the disclosure relates are contemplated as within the scope of the disclosure. In particular, although the disclosure is discussed in terms of a blood glucose meter, it is contemplated that the invention can be used with devices for measuring other analytes and other sample types. Such alternative embodiments require certain adaptations to the embodiments discussed herein that would be apparent to those skilled in the art.

The present disclosure generally concerns a chemistry matrix that is used to determine the concentration of an analyte (such as, for example, glucose) in the presence of related components (such as for example, maltose) and varying levels of unrelated components (such as for example, oxygen). As previously noted, both the presence of maltose and variations in oxygen levels can interfere with the determination of glucose carried out with a variety of electrochemical biosensors. While the chemistry matrix and accompanying methods will be described below with reference to analyzing blood glucose levels, it should be recognized that the chemistry matrix and methods disclosed can be used to analyze other types of analytes as well.

Embodiments of the present disclosure contemplate a new chemistry matrix for use in determining the concentration of an analyte in a biological fluid. Typically, embodiments of the new chemistry matrix composition include a glucose dehydrogenase, nicotinamide adenine dinucleotide, a phenazine derivative, and/or a nitrosoaniline, or derivative thereof. The different embodiments of the chemistry matrix are used with an electrochemical biosensor to determine the concentration of an analyte after a reaction occurs within the biosensor. Embodiments of phenazine derivatives include photochemically stable phenazine derivatives, such as 1-substituted-5-alkyl phenazine quaternary salts. Further embodiments are also contemplated. A method for determining the concentration of an analyte using embodiments of the chemistry matrix disclosed is another aspect of the disclosure. The method can determine, for example, blood glucose levels ranging from about 20 mg/L to about 600 mg/L at test times of about five seconds or less. The chemistry matrix can function well at a pH of from about 6.5 to about 8.5.

The new chemistry matrix will now be fully described in detail. Components of the new chemistry matrix can include an enzyme, a cofactor, a reagent, and a mediator. When employed, the enzyme can be glucose dehydrogenase, the cofactor can be nicotinamide adenine dinucleotide, the reagent can be a phenazine derivative, and the mediator can be a nitrosoaniline. Embodiments of phenazine derivatives include 5-alkylphenazine quaternary salts. It will be understood that nitrosoaniline is an example of an indirect electron mediator in the sense that a nitrosoaniline molecule is not itself directly involved in an electron mediating sequence typically employed in electrochemical analyte detection and measurement methods; rather, nitrosoaniline participates in the sequence by reacting with glucose and other components of the chemistry matrix to produce once or twice removed electroactive reaction product, and it is the electroactive reaction product that is directly involved in the typical mediating sequence, as may be more fully described and explained in U.S. Pat. Nos. 5,122,244 and 5,286,362 (referenced above). Notwithstanding the foregoing, nitrosoaniline and/or its derivatives may be referred to as a mediator herein and in other references created and/or prepared by applicant with the understanding that nitrosoaniline is a precursor to the mediator directly involved in the electrochemical mediator sequence.

Phenazine Derivatives

Although not required, suitable phenazine derivatives are typically chosen such that the derivatives are stable in the presence of light and particularly at a pH range of from about 7 to about 8.5. Suitable phenazine derivatives include 5-alkylphenazine quaternary salts, such as 5-alkyl-1-substituted phenazine quaternary salts of the type illustrated by formulas Ia described above and IIa and IIb provided below:

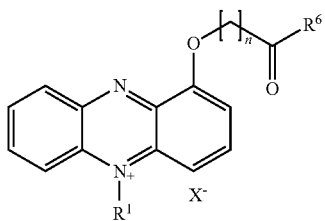

IIa

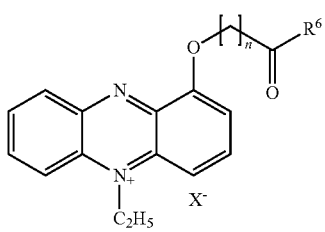

IIb where $R^6$ is selected from the group consisting of —OH, —OR$^1$, —NH$_2$, —NHR$^2$, —NR$^2$R$^3$, —NH(CH$_2$)$_m$NR$_2$, —NH(CH$_2$)$_m$OH, —O(CH$_2$)$_m$NH$_2$, and —O(CH$_2$)$_m$OH, $R^2$ is a $C_1$ to $C_6$ alkyl group, $R^1$ is $C_1$ to $C_6$ alkyl, $R^2$ and $R^3$ are the same or different and each represents a H or a $C_1$ to $C_6$ alkyl group, X⁻ is an anion selected from the group consisting of halide, sulfate, alkyl sulfate, phosphate, phosphite, carboxylate, CF$_3$COO⁻, CH$_3$OSO$_2$⁻, C$_2$H$_5$OSO$_2$⁻, and CH$_3$SO$_3$⁻, and n and m are integers ranging from about 1 to about 6.

Nitrosoanilines

Nitrosoanilines have the general formula III

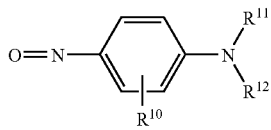

III in which $R^{10}$ denotes hydrogen, halogen, alkoxy or alkylthio, and $R^{11}$ represents an alkyl or a hydroxyalkyl residue and $R^{12}$ represents a hydroxyalkyl residue or $R^{11}$ and $R^{12}$ are the same or different and each represents a dialkylaminoalkyl residue, a hydroxyalkyl, a hydroxyalkoxyalkyl or alkoxyalkyl residue optionally substituted by OH in the alkyl moiety or a polyalkoxyalkyl residue optionally substituted by a hydroxy residue in the alkyl moiety, or $R^{11}$ and $R^{12}$ form an alkylene residue interrupted by sulphur or nitrogen in which nitrogen is substituted by an alkyl, hydroxyalkyl, hydroxyalkoxyalkyl, alkoxyhydroxyalkyl, dioxanylyl-alkyl or polyalkoxyalkyl residue, each of which is itself optionally substituted in the alkyl moiety by a hydroxy residue, or if $R^{10}$ is in the ortho position to NR$^{10}$R$^{11}$, R$^{11}$ also together with R$^{10}$ represents an alkylene residue wherein $R^{12}$ then represents a hydroxyalkyl residue or, if the alkylene residue contains 3 carbon atoms, it also optionally represents an alkyl residue. In this connection halogen denotes fluorine, chlorine, bromine or iodine. Fluorine and chlorine are typical halogens for $R^{10}$. Alkyl, alkoxy or alkylthio are residues with 1-6 carbon atoms, with those containing 1-3 carbon atoms being particularly suitable. The foregoing definition for alkyl also applies to the alkyl moiety in hydroxyalkyl, dialkylaminoalkyl, hydroxyalkoxy-alkyl, alkoxyalkyl, polyalkoxyalkyl, alkoxy-hydroxyalkyl and dioxanylyl-alkyl residues.

A dioxanylyl-alkyl residue is a residue in which a dioxan ring system is bound to an alkyl residue. It is typically a 1,4-dioxan ring system, i.e.

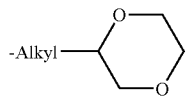

IV

A polyalkoxyalkyl residue is an -alkyl-(alkoxy)$_p$-alkoxy residue in which p equals 1-10. Typically p equals 1-4; and more typically, p equals 1-3.

An alkylene residue is a straight-chained or branched residue, preferably straight-chained and can be either saturated or unsaturated, such as a saturated hydrocarbon chain consisting of 2-5, preferably 2-4, C-atoms with two free binding sites.

Within the meaning of an alkylene residue of $R^{11}$ and $R^{12}$ which is interrupted by sulphur or nitrogen, a thiomorpholine or piperazine residue formed by the inclusion of the nitrogen atom is suitable. The piperazine residue is especially suitable.

Within the meaning of an alkylene residue formed from $R^{11}$ and $R^{12}$, the indoline or 1,2,3,4-tetrahydroquinoline residue formed by the inclusion of the aromatic ring of the general formula V is suitable.

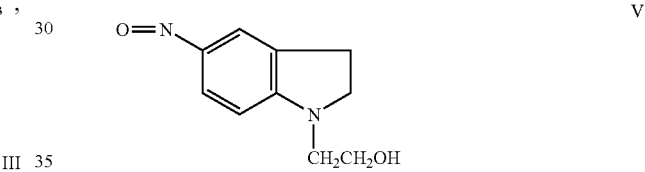

V

As the salt of a nitrosoaniline derivative according to the present disclosure of the general formula III, those of strong acids, in particular mineral acids such as hydrochloric acid, sulphuric acid, nitric acid and phosphoric acid are suitable. Hydrochlorides are especially suitable.

The following new nitrosoaniline derivatives are especially suitable components of the present chemistry matrix:

a) 2,2'-[(3-fluoro-4-nitrosophenyl)imino]bis-ethanol,
b) 2,2'-[(3-chloro-4-nitrosophenyl)imino]bis-ethanol,
c) 2,2'-[(3-methoxy-4-nitrosophenyl)imino]bis-ethanol,
d) 2,2'-[(3-methylmercapto-4-nitrosophenyl)imino]bis-ethanol,
e) 2-[(2-hydroxyethoxy)ethyl-(4-nitrosophenyl)amino]ethanol,
f) 2-[(2-methoxyethoxy)ethyl-(4-nitrosophenyl)amino]ethanol,
g) 1-[N-(2-hydroxyethyl)-(4-nitrosoanilino)]-3-methoxy-2-propanol,
h) 1-[N-(2-hydroxyethyl)-(4-nitrosoanilino)]-3-(2-hydroxyethoxy)-2-propanol,
i) 1-methyl-4-(4-nitrosophenyl)-piperazine,
j) 4-(4-nitrosophenyl)-1-piperazino-ethanol,
k) 5-nitroso-1-indoline ethanol,
l) 1-methyl-6-nitroso-1,2,3,4-tetrahydroquinoline,
m) 6-nitroso-3,4-dihydro-1(2H)quinoline ethanol and their salts
n) 2-[(2-hydroxyethyl-4-nitrosophenyl)amino]ethanol.

Of these the compounds a), d), e), f), g) and h) as well as their salts are particularly suitable. Compound e) or its salts, in particular the hydrochloride, is especially suitable.

Preparation of Phenazine Component

One of the components in the chemistry matrix includes a phenazine derivative. The phenazine derivative can be selected from a variety of different substituted phenazines, however, 5-alkyl, 1-substituted phenazines are useful in this present disclosure, most preferably 5-ethyl-1-substituted phenazines. A variety of different linking groups at position 1 of 5-alkylated phenazine are suitable. Suitable substituted phenazine include structure Ia, provided below:

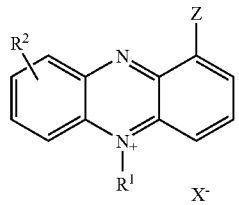

Ia where:
Z is selected from the group consisting of —$(CH_2)_m$COOH, —NHAc, and —OY,
where m is an integer ranging from 0 to about 6 and Y is selected from the group consisting of

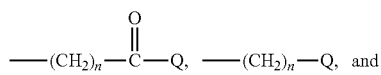

where n is an integer ranging from about 1 to about 4, Q is —OH, —$OR^1$, —$NH_2$, —$NHR^2$, —$NR^2R^3$, —$NH(CH_2)_oNR^2R^3$, —$NH(CH_2)_oOH$, —$NHCH_2CH_2$—$(OCH_2CH_2)_o$-G, —$(CH_2)_oNR^2R^3$, —$OCH_2CH_2)_oNR^2R^3$ and —$(OCH_2CH_2)_oOH$, where G is —COOH, $NR^2R^3$, or

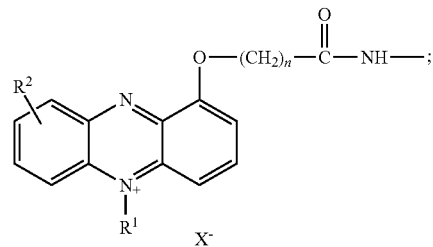

Ib $R^1$ is a $C_1$ to $C_6$ alkyl group, $R^2$ and $R^3$ are the same or different and each represents a H or a $C_1$ to $C_6$ alkyl group, o is an integer ranging from about 1 to about 6; and X is an anion selected from the group consisting of halide, sulfate, alkyl sulfate, phosphate, phosphite, carboxylate, $CF_3COO^-$, $CH_3OSO_2^-$, $C_2H_5OSO_2^-$, and $CH_3SO_3^-$.

An especially suitable phenazine derivative can be illustrated by formula IIa provided below:

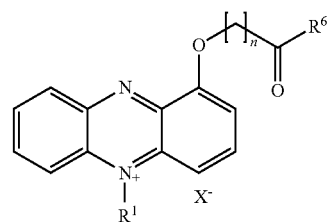

IIa where $R^6$ is selected from the group consisting of —OH, —$OR^2$, —$NH_2$, —$NHR^2$, —$NR^2R^3$, —$NH(CH_2)_mNR_2$, —$NH(CH_2)_mOH$, —$O(CH_2)_mNH_2$, and —$O(CH_2)_mOH$, $R^2$ is a $C_1$ to $C_6$ alkyl group, $R^1$ is $C_1$ to $C_6$ alkyl, $R^2$ and $R^3$ are the same or different and each represents a H or a $C_1$ to $C_6$ alkyl group, $X^-$ is an anion selected from the group consisting of halide, sulfate, alkyl sulfate, phosphate, phosphite, carboxylate, $CF_3COO^-$, $CH_3OSO_2^-$, $C_2H_5OSO_2^-$, and $CH_3SO_3^-$, and n and m are integers ranging from about 1 to about 6.

Reaction schemes 1-9, which follow, illustrate some typical reaction pathways which can be used to prepare suitable phenazine derivatives.

Scheme 1

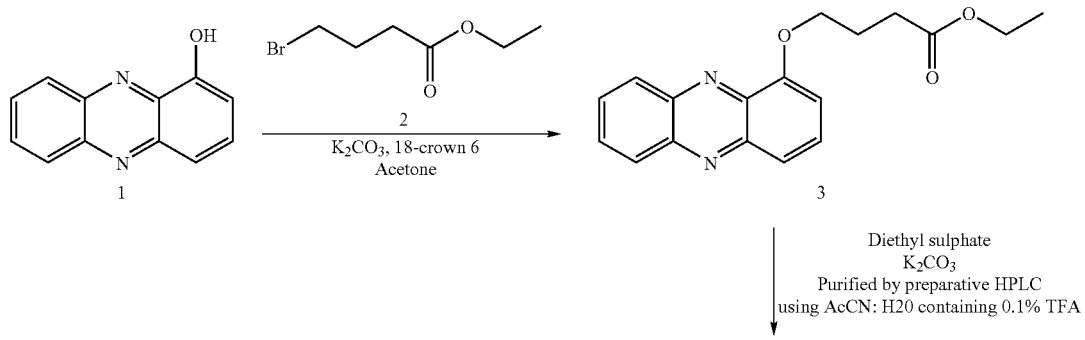

Diethyl sulphate
$K_2CO_3$
Purified by preparative HPLC
using AcCN: H20 containing 0.1% TFA 13 14

-continued

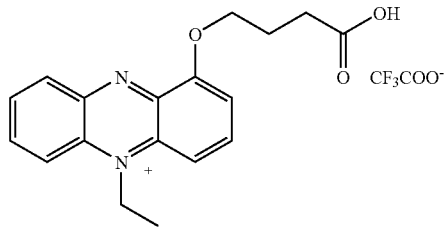

5

⟵ 0.1N HCl
37° C., 5 days
Purified by
preparative HPLC using
AcCN: H20 containing
0.1% TFA

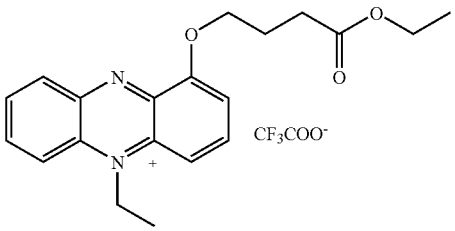

4

Scheme 1 represents the synthesis of the 5-ethyl-1-alkoxy carboxylic acid phenazine derivative (5). The preparation of this compound is described in the literature [see Eur. J. Biochem, 179, 293-298 (1989)]. However, the synthetic procedure was extensively modified to provide the necessary quantities of the substituted phenazine (5).

1-Hydroxyphenazine (1) was purchased from TCI America. This was reacted with ethyl 4-bromobutyrate in the presence of potassium carbonate and 18-crown 6 in acetone under reflux conditions to give phenazine ethyl ester (3). The reaction of phenazine ethyl ester (3) with diethylsulfate as described in the literature did not provide any N-alkylated product. The reaction process for N-ethylation of phenazine ethyl ester (3) was investigated by adding a base, such as potassium carbonate. Thus, reaction of phenazine ethyl ester (3) with diethylsulfate in the presence of potassium carbonate at 100° C. for 18h provided the 5-N-ethyl 1-substituted carboxylic acid ethyl ester phenazine derivative (4). The resulting 5-N-ethyl phenazine ethyl ester was hydrolyzed by dilute hydrochloric acid to achieve the 5-ethyl-1-carboxybutyl phenazine derivative (5).

Scheme 2

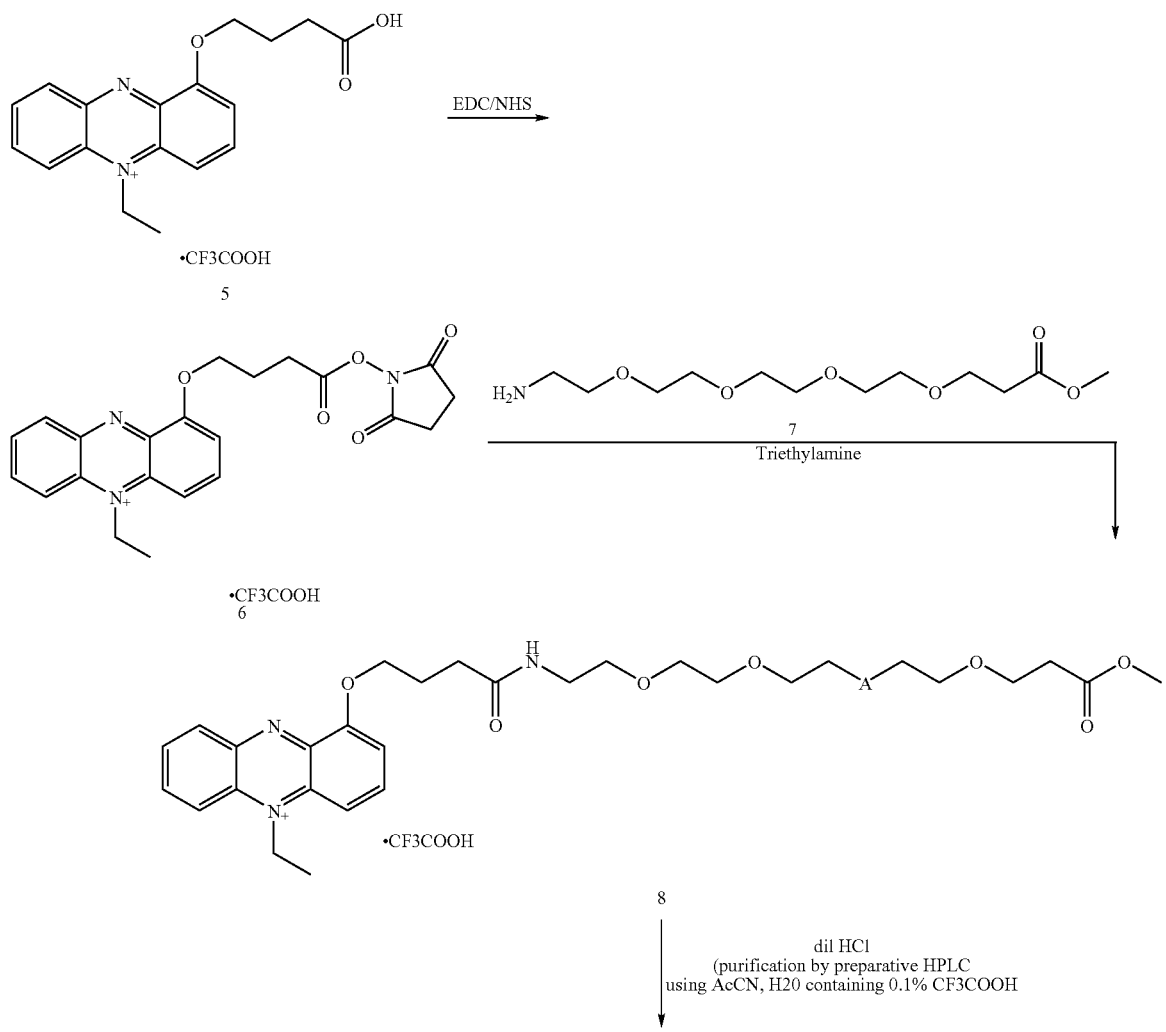

-continued

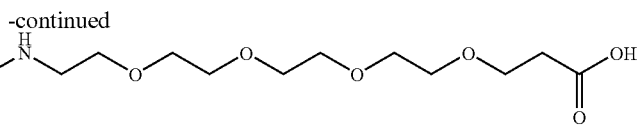
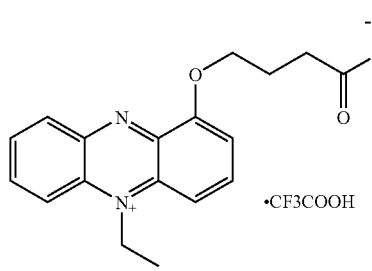

•CF3COOH

9

Scheme 2 represents the synthesis of a 1-alkoxy-substituted phenazine derivative (9) having a hydrophilic linker which can affect the phenazine's solubility. The availability of hydrophilic substituted phenazines allows for a greater range of matrix formulations. The 5-N-ethyl phenazine 1-hydoxybutyric acid derivative (5) is reacted with 1-Ethyl N-3,3-dimethylaminopropyl carbodiimide and N-hydroxysuccinimide to give corresponding N-hydroxysuccinimide. This activated ester is reacted with the commercially available amino d-PEG$_4$ methyl ester (Quanta Biodesign, USA) in the presence of a tertiary base, such as triethylamine. Deprotection of a methyl ester is described in the literature (see Greene, T. and Wuts, P., "Protective Groups in Organic synthesis", 2$^{nd}$ edition, Wiley Intersciences, 1991). The methyl ester group can be deprotected in the presence of an acid or a base to give phenazine derivative (9) with a PEG linker. Hydrolysis of the methyl ester with dilute hydrochloric acid has proven particularly suitable in this phenazine chemistry system.

Scheme 3

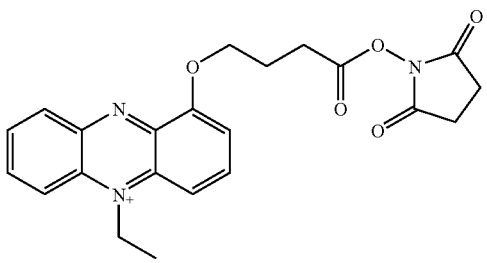

6

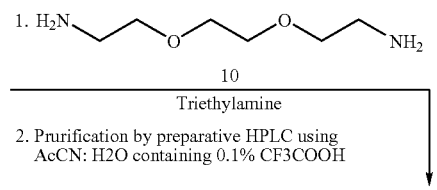

10

Triethylamine

2. Prurification by preparative HPLC using AcCN: H2O containing 0.1% CF3COOH

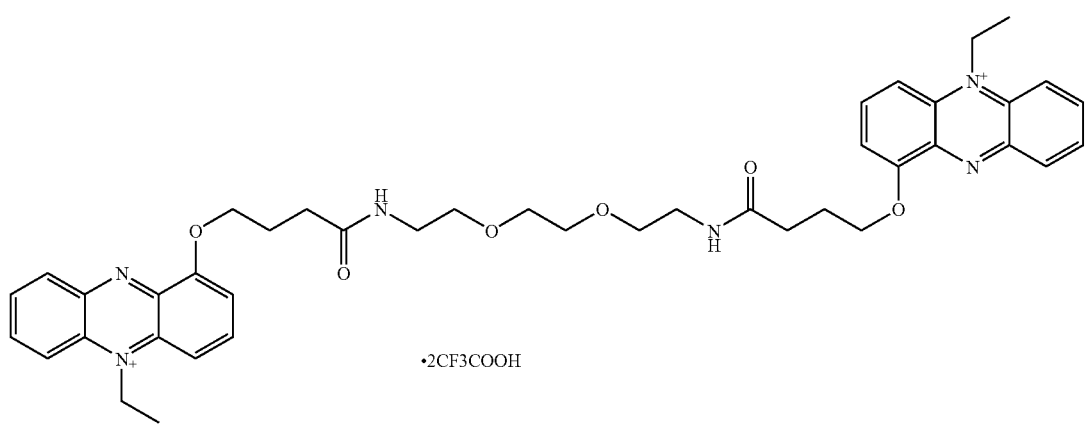

•2CF3COOH

11

Scheme 3 describes the synthesis of a dimerized phenazine derivative (11). A chemistry matrix including phenazine derivative (11) typically provides improved sensitivity. Phenazine derivative (11) can be prepared by reacting the activated ester (6) with 2,2-(ethylenedioxy)bis ethylamine (Aldrich Chemical Company, USA), in the presence of a tertiary base such as triethylamine or diisopropylethylamine and in a solvent such as dimethylformamide or tetrahydrofuran at a temperature ranging from 0° C. to room temperature. Particularly suitable base/solvent combinations include triethylamine/dimethylformamide.

Scheme 4 illustrates the synthesis of an amino terminated 1-substitited N-ethyl phenazine. O-Alkylation of 1-hydroxyphenazine can be carried out using a terminal amino protected alkylating agent, such as for example, a phthalimido or a t-BOC derivative. The resulting t-Boc protected amine can be deprotected under acidic conditions, such as trifluoroacetic acid, whereas the resulting phthalimido protected amine can be deprotected in the presence of hydrazine or methylamine. A particularly suitable method includes reacting 1-hydroxyphenazine with N-(4-bromobutyl)phthalimide (Acros Chemicals, USA), in the presence of a base, such as

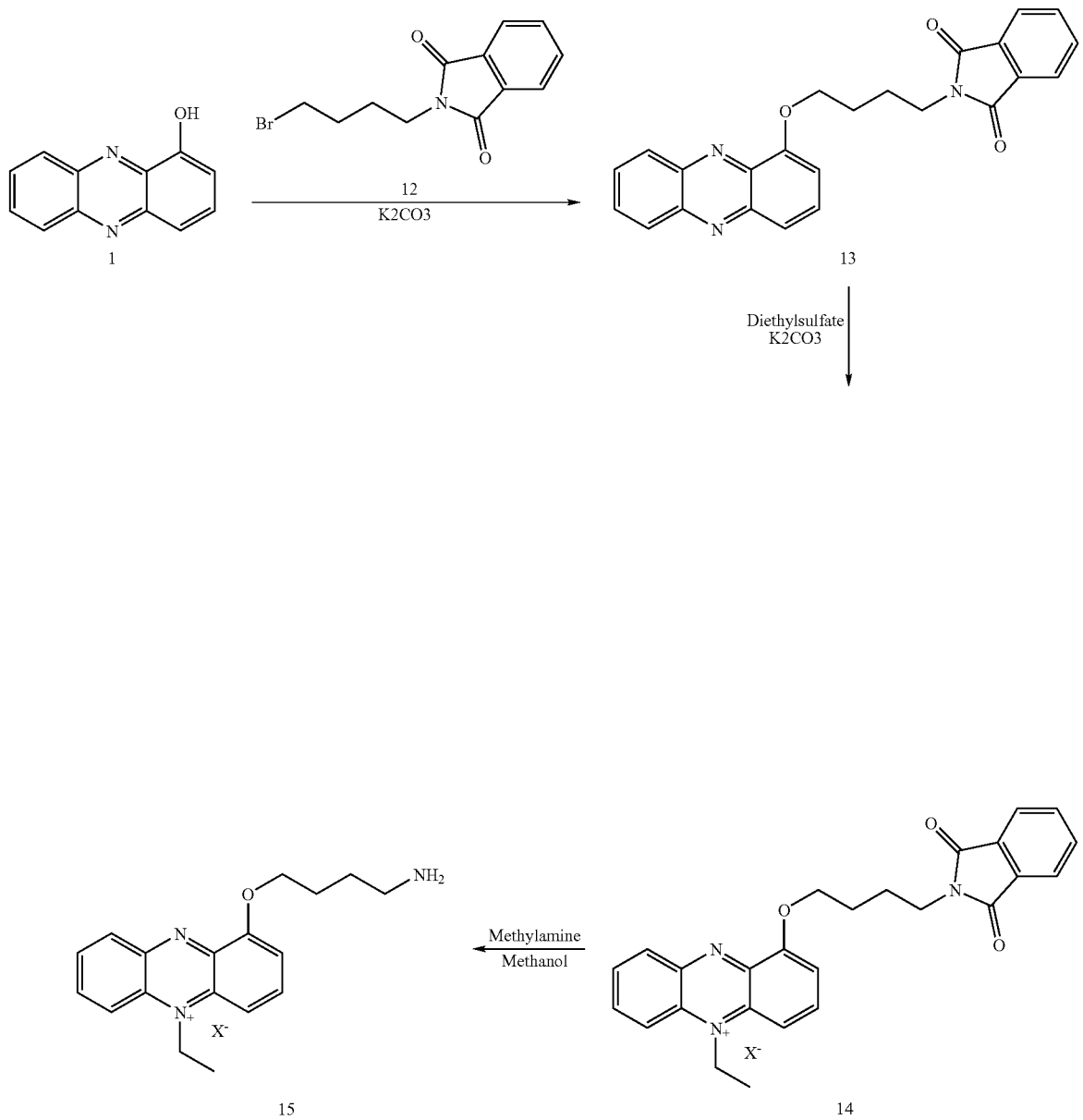

potassium carbonate in a solvent such as acetone, DMF, or THF under reflux conditions. Acetone has been found to be a particularly suitable solvent for this reaction. The resulting alkylated product (13) is reacted with diethylsulfate in the presence of potassium carbonate to give N-ethyl phthalimido protected phenazine (14). The phthalimido group is deprotected with methylamine in methanol at room temperature to give amino terminated 1-substituted N-ethyl phenazine (15).

Scheme 5

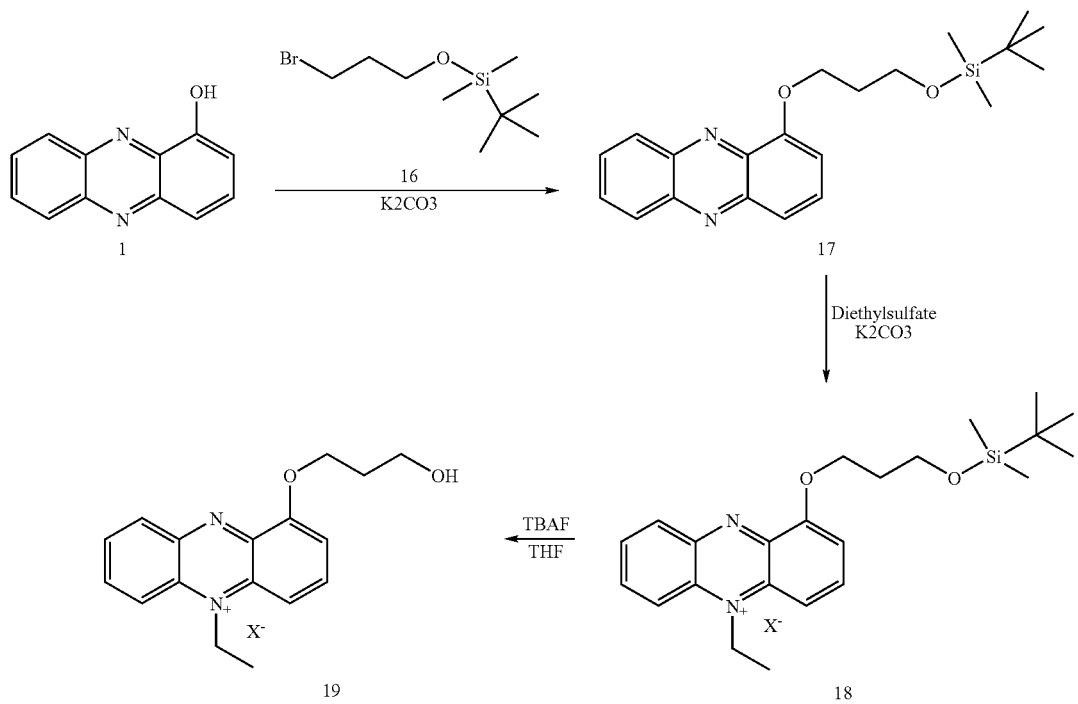

Scheme 5 describes the synthesis of a hydroxyl terminated 1-substituted phenazine derivative. 1-Hydroxy phenazine (1) is reacted with a hydoxy protected alkylating agent, such as for example, (3-bromopropoxy)-tert-butyldimethylsilane (16), (Aldrich chemical company, USA) in the presence of potassium carbonate in acetone under reflux conditions to give the tert-butyldimethylsilane (TBDMS) protected phenazine derivative (17). N-alkylation of (17) is performed with diethylsulfate in the presence of potassium carbonate to give N-ethyl 1-substituted protected hydroxyl terminated phenazine derivative (18). Deprotection of TBDMS group is performed in the presence of tetrabutylammonium fluoride (TBAF) in THF at room temperature to give 1-hydroxybutyl N-ethyl phenazine (19).

Scheme 6

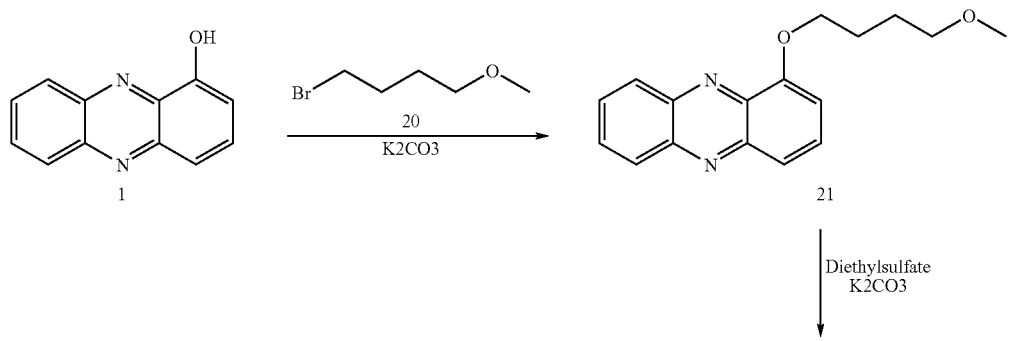

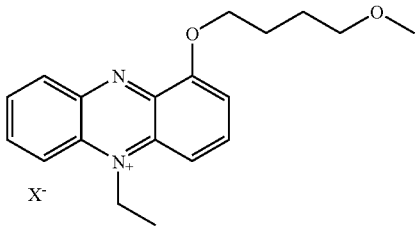

22

Scheme 6 illustrates the synthesis of N-ethyl phenazine 1-hydroxybutyl methyl ether. The phenazine ether (21) is prepared by the alkylation of the 1-hydroxyphenazine (1) with 4-methoxybutylbromide (Aldrich Chemical Company, USA) to give phenazine derivative (21). N-ethyl phenazine (22) is prepared by reaction of compound (21) with diethyl sulfate in the presence of potassium carbonate.

poured over into 2N HCl to give N-phenyl-3-nitro anthranilic acid (25a) or the methyl substituted derivative (25b). Intermediates (25a) or (25b) are reacted with sodium borohydride in 2N NaOH solution under reflux conditions to effect ring closure and provide the sodium salt of a phenazine, which, upon acidification, provides (26a) or (26b). The acid chloride of the phenazine 1-carboxy derivative (or 8-methyl 1-carbox-

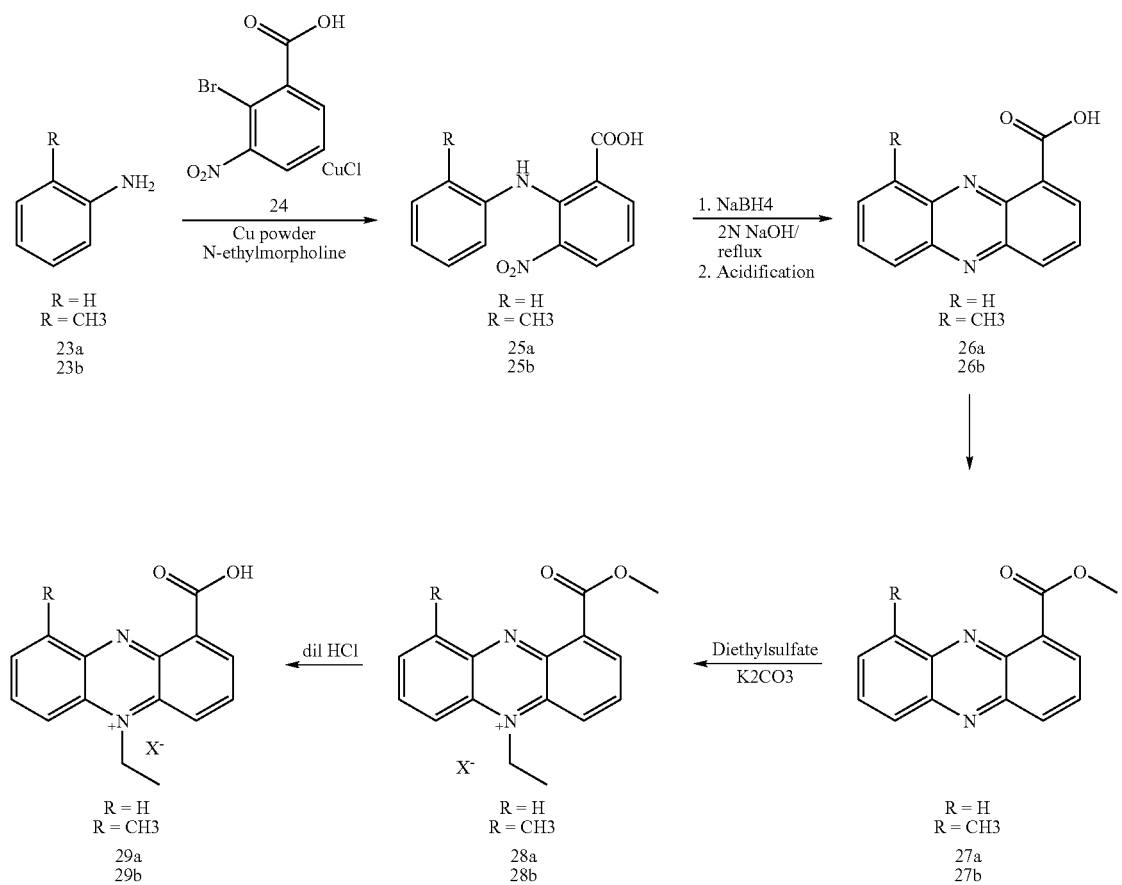

Reaction scheme 7 illustrates the synthesis of a 1-carboxy N-ethyl phenazine (29a) and 8-methyl 1-carboxy N-ethyl phenazine (29b) derivative. A mixture of aniline (or ortho toluidine) and 2-bromo-3-nitrobenzoic acid is reacted in the presence of CuCl, Cu powder and N-ethylmorpholine in butane-2,3-diol at 70 to 80° C. for 8 to 24 hours. This reaction mixture is diluted with 0.1 M $NH_4OH$ solution and filtered through a bed of celite. The resulting solution is slowly yphenazine) is prepared by the reaction with thionyl chloride and the resulting acid chloride is converted to methyl ester by the reaction with methanol in HCl. The resulting phenazine methyl ester (27a) or (27b) is alkylated with diethyl sulfate and potassium carbonate to give corresponding N-ethyl phenazine derivatives (28a) or (28b). Finally, the methyl ester group of phenazines (28a) or (28b) is hydrolyzed with dilute hydrochloric acid to give (29a) or (29b).

Scheme 8

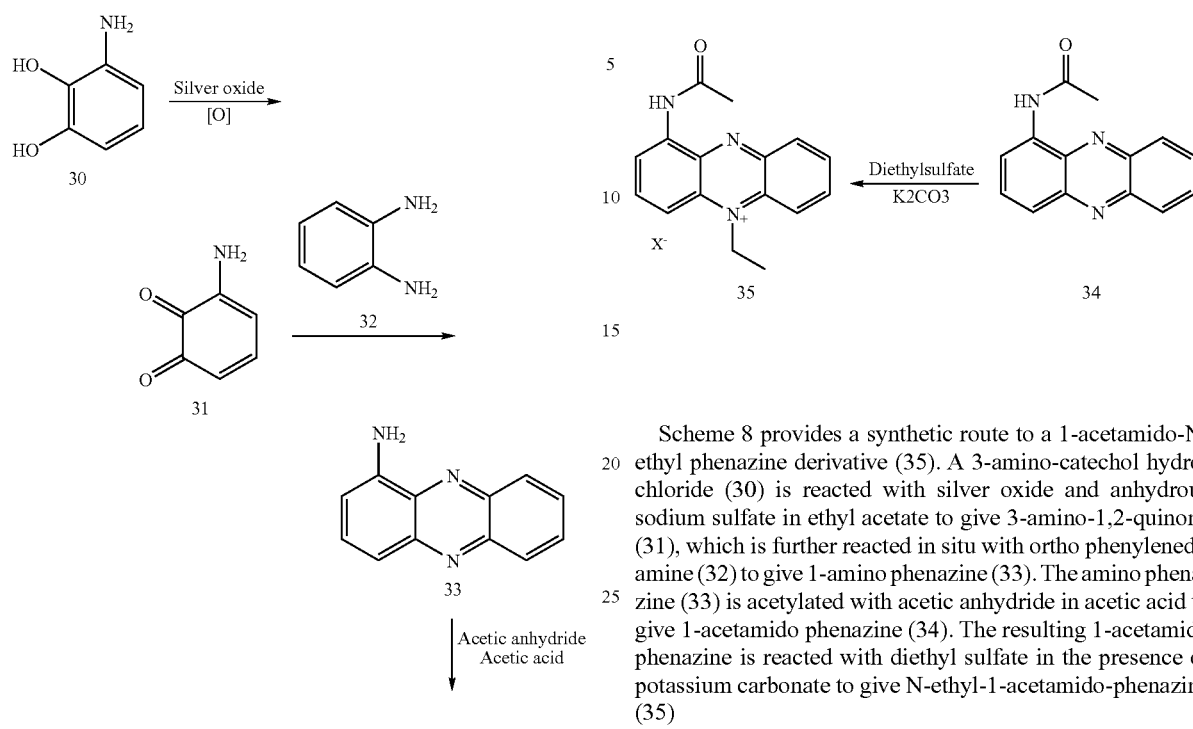

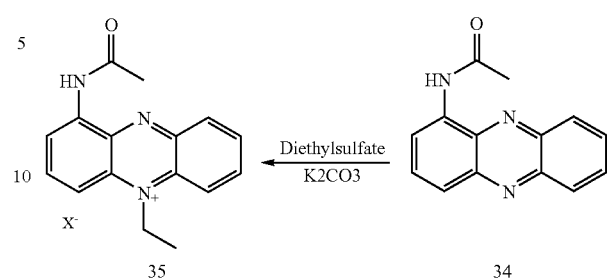

Scheme 8 provides a synthetic route to a 1-acetamido-N-ethyl phenazine derivative (35). A 3-amino-catechol hydrochloride (30) is reacted with silver oxide and anhydrous sodium sulfate in ethyl acetate to give 3-amino-1,2-quinone (31), which is further reacted in situ with ortho phenylenediamine (32) to give 1-amino phenazine (33). The amino phenazine (33) is acetylated with acetic anhydride in acetic acid to give 1-acetamido phenazine (34). The resulting 1-acetamido phenazine is reacted with diethyl sulfate in the presence of potassium carbonate to give N-ethyl-1-acetamido-phenazine (35)

Scheme 9

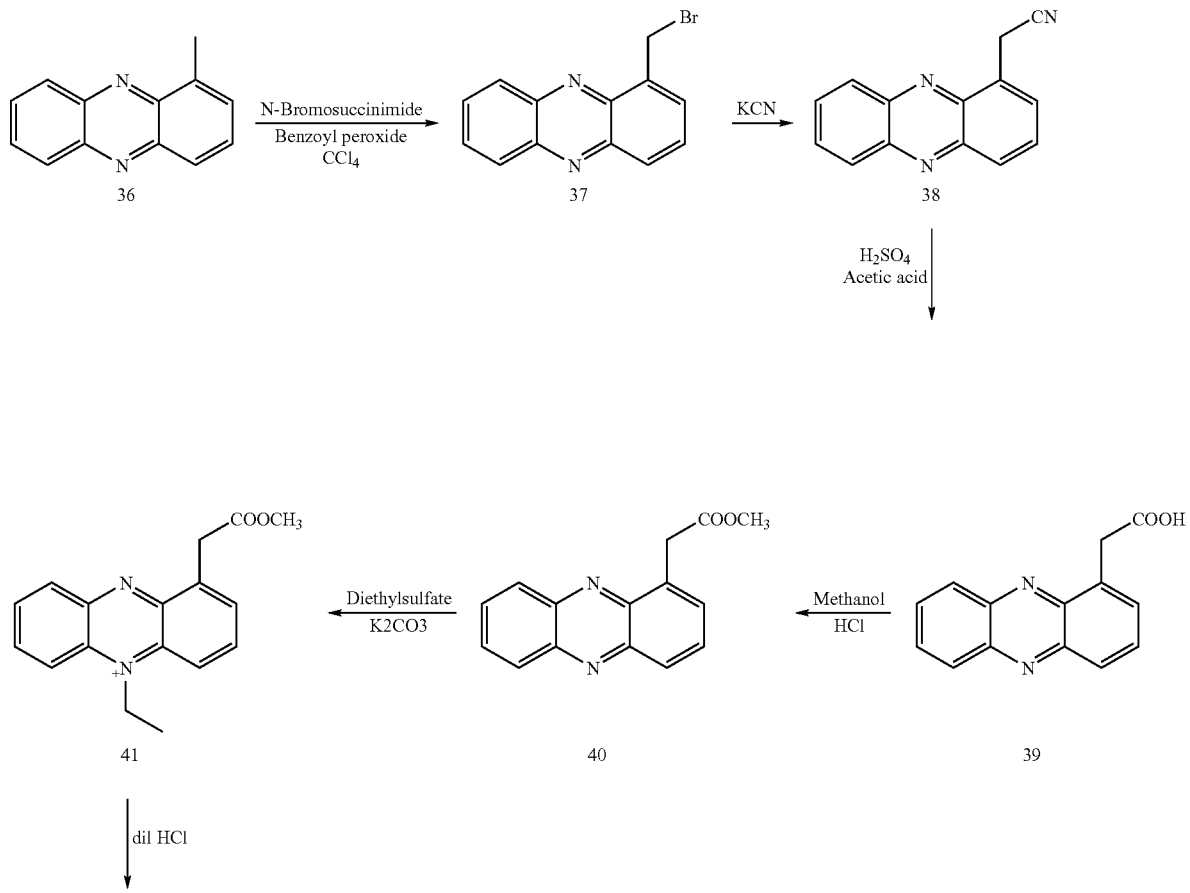

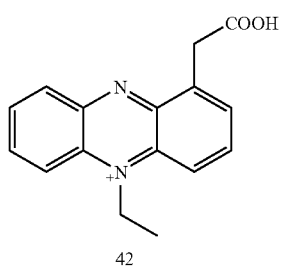

42

Scheme 9 provides a synthetic route to the 1-carboxymethyl-5-N-ethyl phenazine derivative (42). The bromo derivative (37) is formed by reacting 1-methyl phenazine (36) (available from Apin Chemicals, UK) with N-bromosuccinimide in the presence of benzoyl peroxide and a solvent. Carbon tetrachloride is a particularly suitable solvent for the bromination reaction. Reaction of the bromide (37) with KCN in a suitable solvent, such as, for example, DMF, gives the 1-cyanomethyl phenazine derivative (38). Acid hydrolysis of the cyanophenazine (38) provides the 1-carboxymethyl phenazine (39). The acid group of compound (39) is converted to a methyl ester by reaction with methanol and HCl to give the phenazine ester (40). Ester (40) can be N-alkylated with dimethyl sulfate in the presence of potassium carbonate to give the 5-ethyl phenazine ester (41). Hydrolysis of the ester (41) with dilute hydrochloric acid provides the 5-ethyl-1-carboxymethyl phenazine (42).

Preparation of Nitrosoaniline Component

The compounds of the general formula III can be produced by reacting a compound of the general formula VI, in which $R^4$, $R^5$ and $R^6$ have the same meaning as in compounds of the general formula III, with nitrite. Details concerning formula III are provided above.

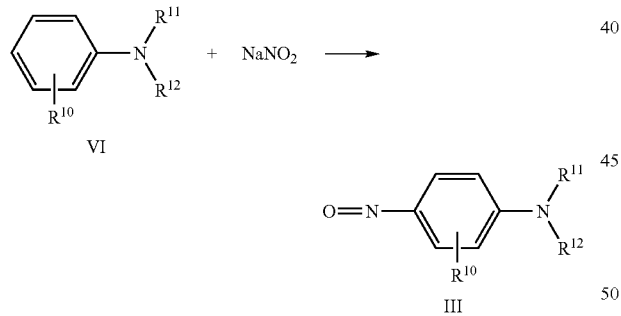

An analogous process is known from J. J. D'Amico et al., J. Amer. Chem. Soc. 81, 5957 (1959).

Alkali nitrite is typically used as the nitrite, in which lithium, sodium, potassium, rubidium or cesium is possible as the alkali metal; sodium nitrite and potassium nitrite are particularly suitable. Sodium nitrite is especially suitable. The reaction typically takes place in an acid medium at low temperature. It is advantageous when the temperature is below 10° C., preferably between −10 and +5° C.

It is advantageous when the reaction of a compound of the general formula VI with nitrite takes place in an aqueous medium. A suitable pH for the medium is less than 3, and less than 2 is particularly suitable.

In a one embodiment for the reaction, a compound of the general formula VI or a salt thereof, such as a salt of a mineral acid such as hydrochloric acid, sulphuric acid, nitric acid or phosphoric acid, is first added to an aqueous acidic medium and cooled.

Then, nitrite, typically in a dissolved form, is added while maintaining the reaction mixture at a low temperature. It is advantageous when an aqueous medium is also used as the solvent for the nitrite. After addition of the nitrite the reaction mixture is kept at a low temperature until the reaction is completed. In order to process the reaction mixture it is typically extracted with an organic solvent and the product is isolated from the extract.

Chemistry Matrix

A first embodiment of the chemistry matrix includes glucose dehydrogenase, nicotinamide adenine dinucleotide, a 5-ethyl phenazine quaternary salt, and a nitrosoaniline. Although not required, suitable quaternary salts are typically photochemically stable. Examples of photochemically stable 5-ethyl quaternary salts are illustrated by formula Ia and IIb:

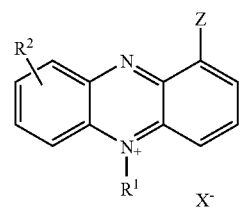

Ia where:

Z is selected from the group consisting of —$(CH_2)_m$COOH, —NHAc, and —OY, where m is an integer ranging from 0 to about 6 and Y is selected from the group consisting of

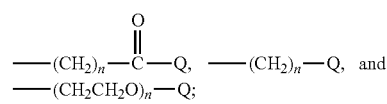

where n is an integer ranging from about 1 to about 4, Q is —OH, —$OR^1$, —$NH_2$, —$NHR^2$, —$NR^2R^3$, —$NH(CH_2)_o$$NR^2R^3$, —$NH(CH_2)_oOH$, —$NHCH_2CH_2$—$(OCH_2CH_2)_o$-G, —$(CH_2)_oNR^2R^3$, —$OCH_2CH_2)_oNR^2R^3$ and —$(OCH_2CH_2)_o$OH, where G is —COOH, $NR^2R^3$, or

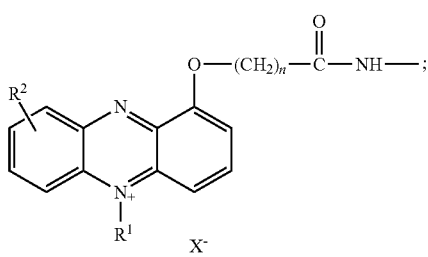

$R^1$ is a $C_1$ to $C_6$ alkyl group, $R^2$ and $R^3$ are the same or different and each represents a H or a $C_1$ to $C_6$ alkyl group, o is an integer ranging from about 1 to about 6; and X is an anion selected from the group consisting of halide, sulfate, alkyl sulfate, phosphate, phosphite, carboxylate, $CF_3COO^-$, $CH_3OSO_2^-$, $C_2H_5OSO_2^-$, and $CH_3SO_3^-$; and

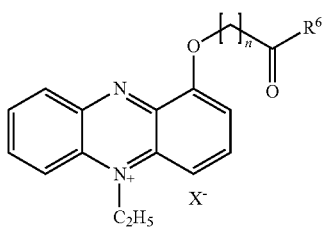

where $R^6$ is selected from the group consisting of —OH, —$OR^2$, —$NH_2$, —$NHR^2$, —$NR^2R^3$, —$NH(CH_2)_mNR_2$, —$NH(CH_2)_mOH$, —$O(CH_2)_mNH_2$, and —$O(CH_2)_mOH$, $R^2$ is a $C_1$ to $C_6$ alkyl group, $R^2$ and $R^3$ are the same or different and each represents a H or a $C_1$ to $C_6$ alkyl group, $X^-$ is an anion selected from the group consisting of halide, sulfate, alkyl sulfate, phosphate, phosphite, carboxylate, $CF_3COO^-$, $CH_3OSO_2^-$, $C_2H_5OSO_2^-$, and $CH_3SO_3^-$, and n and m are integers ranging from about 1 to about 6.

A further embodiment of the chemistry matrix includes a phenazine alkyl quaternary salt having the formula illustrated in formulas IIa or IIb, provided above. Suitable quaternary salts are typically photochemically stable and stable at a pH of from about 6.5 to about 8.5. Additional components of this embodiment can include glucose dehydrogenase, nicotinamide adenine dinucleotide and/or a nitrosoaniline. Suitable nitrosoanilines are represented by formula III, provided above.

A still further embodiment of the chemistry matrix includes glucose dehydrogenase, nicotinamide adenine dinucleotide, a 5-ethyl phenazine quaternary salt represented by formula IIb provided above, and a 1,4-nitrosoaniline represented by formula VII.

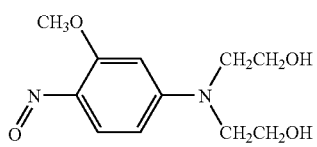

Suitable phenazine quaternary salts are typically photochemically stable.

A still further embodiment of the chemistry matrix composition includes a photochemically stable 5-alkyl phenazine quaternary salt. The composition can additionally contain glucose dehydrogenase, nicotinamide adenine dinucleotide, and a nitrosoaniline. Suitable phenazine quaternary salts are represented by formula I, provided above. Suitable nitrosoanilines are represented by formula III, provided above.

Another embodiment includes a method or test for determining the concentration of an analyte sample (particularly, glucose in blood) utilizing embodiments of the chemistry matrix. The method includes using a biosensor and test strip configuration as previously described. The chemistry matrix is used in a chemical reaction to determine the concentration of the analyte. Certain methods utilize a chemistry matrix that includes glucose dehydrogenase, nicotinamide adenine dinucleotide, a 5-alkyl phenazine quaternary salt, and a nitrosoaniline. Certain other methods utilize a 5-alkylphenazine quaternary salt represented by formula IIb and yet other methods utilize a nitrosoaniline represented by formula VII. The method described herein can be used to analyze samples containing from about 20 mg/L to about 600 mg/L of blood glucose in a test time of about 5 seconds or less. Optimum results can be obtained upon utilizing the chemistry matrix within a pH range of from about 6.5 to about 8.5.

Figure 2:
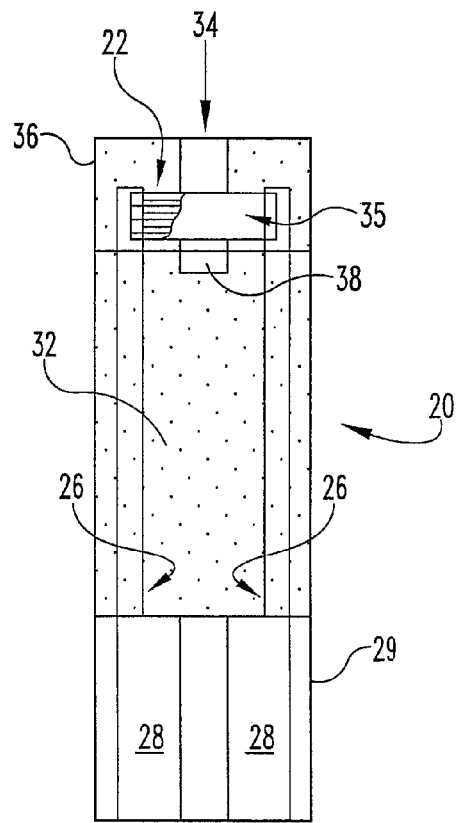
FIG. 2 is a second top view of the FIG. 1 test strip with the cover layer in place.

Reference to the drawings further discloses aspects of the present disclosure. An amperometric electrochemical analyte sensor 20, suitable for use with the chemistry and methods described herein, is illustrated in FIGS. 1 and 2. It should be recognized that the sensor 20 in FIGS. 1 and 2 is merely an example of a type of sensor that can be used in conjunction with the chemistry and method according to the present disclosure, and that other types of sensors with different configurations can similarly be used. For example, although the sensor illustrated in FIGS. 1 and 2 has electrodes formed in an interdigitating array, sensors having a different configuration or with additional electrodes can be used with the disclosed chemistry matrix and method. As another example, the electrodes in the illustrated embodiment have a co-planar configuration, but it should be appreciated that the electrodes 22 in other embodiments can have other configurations, such as a facing construction. For the sake of brevity as well as clarity, not all of the features of the sensor system will be described in detail below, but reference is made to examples of other types of sensors with which the inventive chemistries and methods are useful, including those described in U.S. Pat. No. 5,989,917; 6,270,637; and U.S. Published Application No. 2003/0155237 A1, all of which are hereby incorporated by reference in their entireties.

Turning now to FIG. 1, the sensor 20 includes an interdigitated array of electrodes 22 disposed on flexible substrate 24. One of the electrodes 22 in the pair acts as a working electrode, and the other electrode acts as a counter electrode. However, as indicated before, the electrodes 22 in accordance with one embodiment of the present disclosure can switch roles. That is, an electrode 22 at one time may act as a working electrode and may at another time act as a counter electrode. In the illustrated embodiment, two electrodes 22 are shown, but it should be recognized that the sensor 20 in other embodiments can include more electrodes. The electrodes 22 are connected to electrically-conductive connectors 26 that include contact pads 28 located on the surface of the flexible substrate 24, where the contact pads 28 are available to be contacted to an external electronic circuit, such as a meter. The connectors 26 also include connector portions 30, which connect electrode elements at the array 22 to the pads 28 and which may typically be covered by an insulating layer.

Referring to FIG. 2, non-conductive spacer layer 32 is disposed over the substrate 24 and connector portions 30 of the connectors 26. The spacer layer 32 defines a capillary sample chamber 34, and the sample chamber 34 has an inlet opening in which the fluid sample is drawn into the sample chamber 34. A reagent layer 35 is disposed over the array 22 within the sample chamber 34. The reagent layer 35 will be described in further detail below but is configured to analyze the fluid sample. Foil 36 covers the spacer 32 and a portion of capillary chamber 34 except for an air vent 38, which is used to vent air from the chamber 34.

Preparation of Matrix Solutions

Standard Matrix Solution

A stock buffer solution was prepared by adding 25.148 g of Pipes sesquisodium salt, 0.125 g of Triton X-100, and 2.40 g of Trehalose to 400 mL of double distilled water and adjusting the solution's pH to 7.00. This solution was added to a 500 mL volumetric flask and diluted with double distilled water to make 500 mL of solution. Preparation of the buffer/polymer solution was completed by combining 396 grams of the initial buffer solution with 2 g of polyethylene oxide (300K) and 2 g of Natrosol 250M. Upon standing overnight all solids had dissolved and the solution was ready for use.

A matrix solution was prepared from the stock buffer solution by: (a) adding the following ingredients to a 25 mL speed mixing cup containing 11.198 g of the buffer stock solution in a serial fashion and speed mixing for 1 minute at 33,000 rpm after each addition: 0.5592 g of KCl, 0.1824 g of NAD grade 1 and 0.0913 g of the substituted nitrosoaniline (Structure VII); (b) adjusting the pH to 7.00; and (c) adding 0.0163 g of 1-(3-carboxypropyloxy)-5-ethylphenazine (5 from Scheme 1) to container mixing for 1 minute at 33,000 rpm and finally, add 0.6574 g of glucose dehydrogenase enzyme and speed mixing for 2 minute at 33,000 rpm.

Additional Matrix Solutions Utilizing Alternative Phenazines

Matrix solutions can similarly be prepared utilizing the method provided above by substituting alternative 1-substituted phenazine derivatives for 1-(3-carboxypropyloxy)-5-ethyl phenazine or by similarly substituting alternative nitrosoanilines for the nitrosoaniline represented by formula VI. Suitable phenazine derivatives are typically photochemically stable. Although 1-ethyl-5-substituted phenazine quaternary salts illustrated by formula II can be more suitable, other 1-alkyl-5-substituted phenazine quaternary salts illustrated by formula I, can also be utilized.

Additional Matrix Solutions Utilizing Alternative Nitrosoanilines

Matrix solutions can also be prepared by the method provided above by substituting nitrosoanilines represented by formula III for the nitrosoaniline represented by formula VII.

Preparation of Test Strips

Cards of ACCU-CHEK® Aviva brand electrodes with spacer and capillary design were charged with about 1.8 μL of the basic matrix solution described above in each electrode channel and dried at about 45° C. for about 1 minute. The dried cards were stored in a dry atmosphere overnight and strips of hydrophilic top foils were manually laminated onto the spacer layer. The cards were cut into appropriate strips and stored in desiccated vials until used. This method can similarly be used to prepare test strips based on the several matrix solutions described above.

Examination of Whole Blood Dose Responses

Whole blood samples containing seven different levels of glucose (about 50 to about 600 mg/dL) were measured utilizing the test strips prepared above from the basic matrix solution utilizing about a 2.5 second delay and about a 2.5 second read, meaning that a signal was applied about 2.5 seconds after contacting the sample with the test strip and a reading was taken about 2.5 seconds after application of the signal. The mean current was measured at about 5 seconds after contacting the sample with the test strip to provide a linear relationship between current and glucose concentration. The establishment of a linear relationship between glucose concentration and current read facilitates utilization of the chemistry matrix to analyze an analyte such as glucose. The results are provided in FIG. 3. Similar results are obtained utilizing test strips prepared from the several matrix solutions described above.

Matrix Performance at Different Oxygen Levels

Blood glucose samples having glucose levels ranging from about 0 to about 110 mg/dL were saturated with oxygen at about 39 mm Hg and at about 100 mm Hg of oxygen and the glucose levels determined using the test strips described above prepared from the basic matrix solution. The samples were run with about a 3 second delay and about a 2 second read. The mean current at about 5 seconds was determined and plotted. Neither oxygen level affected the glucose measurement as illustrated in the plot provided in FIG. 4. Similar results are obtained upon repeating this example with test strips prepared from the alternative matrix solutions described above.

Figure 5:
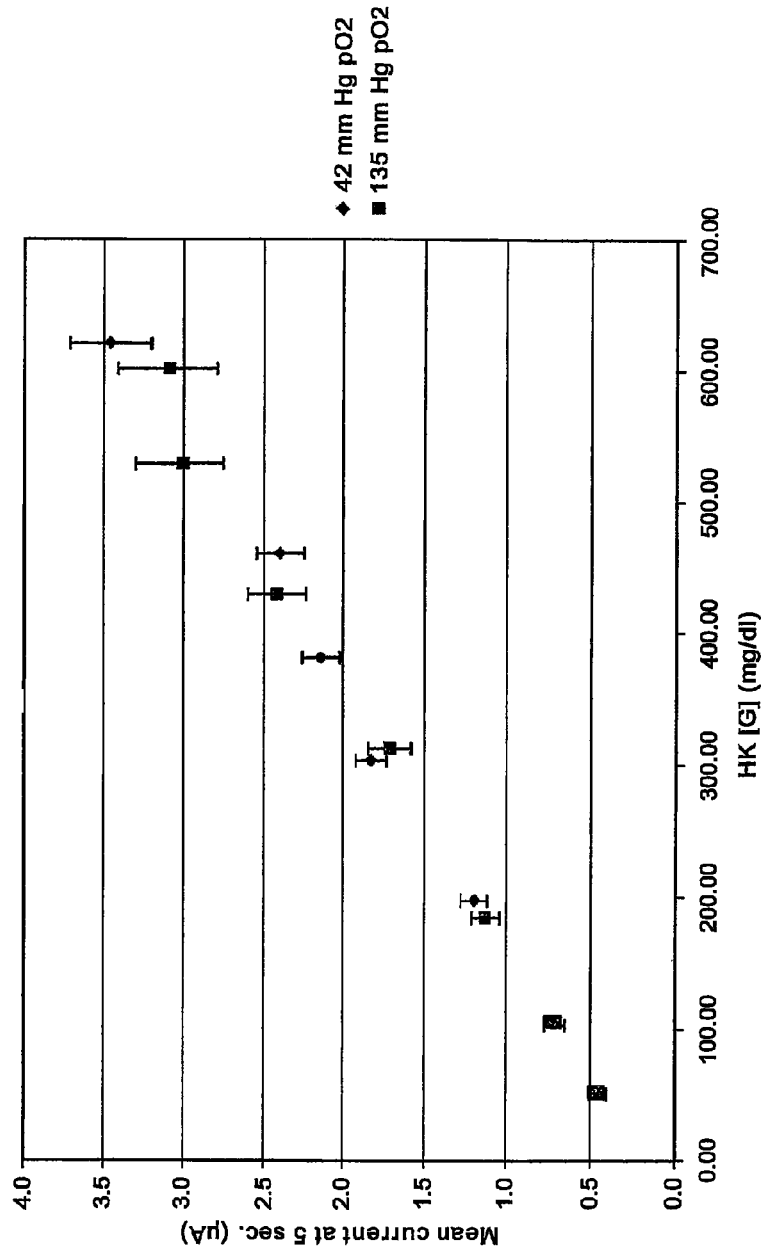
FIG. 5 is a plot illustrating the lack of oxygen interference at two oxygen levels and at glucose levels ranging from about 0 to about 700 mg/dL.

In a subsequent test, blood samples having glucose levels ranging from about 50 to about 600 mg/L were saturated with oxygen at about 42 mm Hg and about 135 mm Hg of oxygen and the glucose levels measured using the test strips prepared above from the basic matrix solution. Neither oxygen level affected the glucose measurement over this wider concentration range as illustrated in FIG. 5. Similar results are obtained upon repeating this example with test strips prepared from the alternative matrix solutions described above.

Maltose Interference Studies

Figure 6:
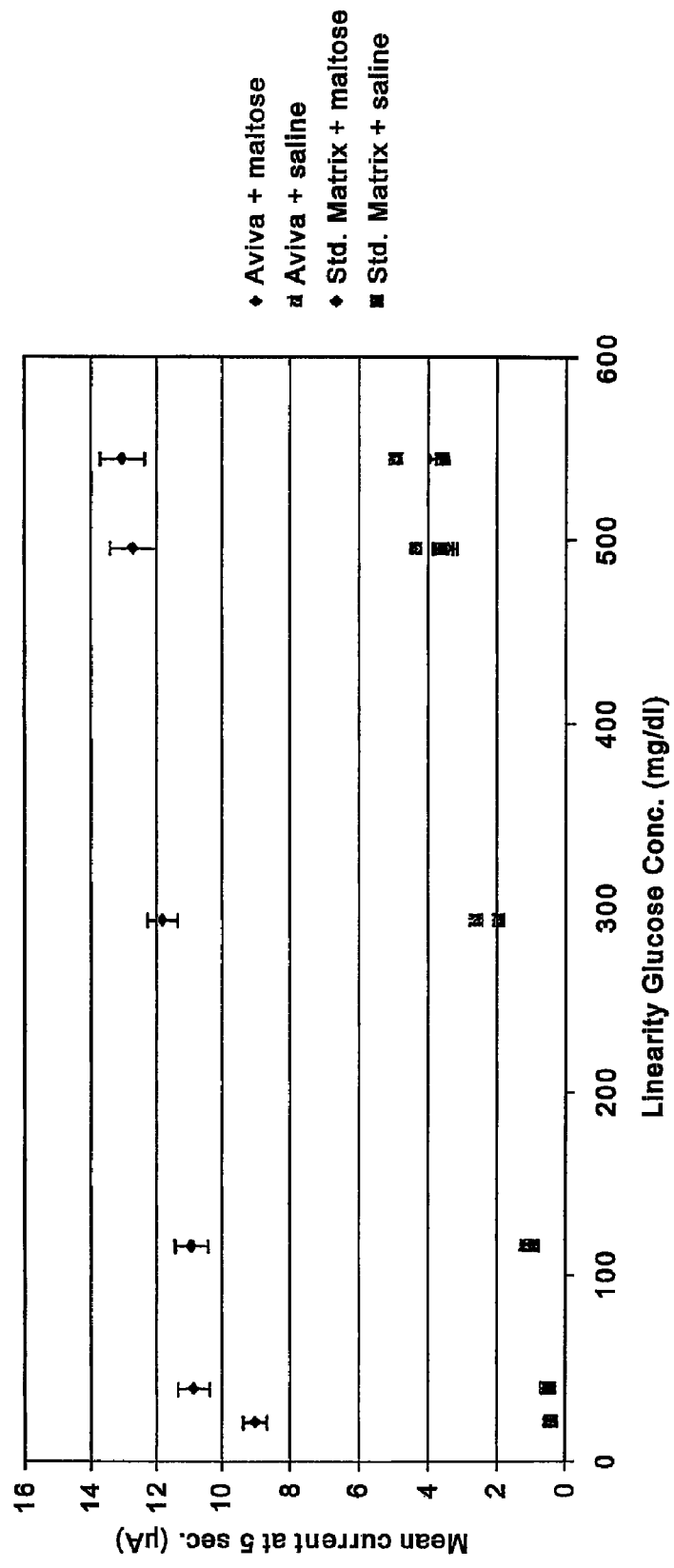
FIG. 6 is a plot illustrating the interference of maltose using a conventional test strip and the absence of interference with a test strip based on the new chemistry matrix.

A maltose stock solution was prepared by adding 21 mM of maltose to 200 mL of saline solution. Six blood samples containing glucose levels ranging from about 10 to about 550 mg/L were prepared. Each sample was split into two portions and to one series of samples was added 0.05 mL of a maltose stock solution for each 1 mL portions of test sample. To the second series of samples, an equal volume of a saline solution was added to 1 mL portions of the test sample. The glucose content of the samples was determined with a standard ACCU-CHEK®Aviva brand test strip and a test strip having generally similar structural elements, but containing the new chemistry matrix described above. As illustrated in FIG. 6, maltose inflated the measurements made with the standard ACCU-CHEK® Aviva brand strip, whereas the determinations made with the new chemistry matrix were substantially the same as samples that did not contain maltose. Similar results are obtained upon repeating this study with test strips prepared from the alternative matrix solutions described above. ACCU-CHEK® and Aviva are registered U.S. trademarks of Roche Diagnostics Gmbh CORPORATION FED REP GERMANY, Sandhofer Strasse, 116 Mannheim FED REP GERMANY D-68305.

While the disclosure has been illustrated and described in detail in the figures and foregoing description, the same is to be considered as illustrative and not restrictive in character, it being understood that only selected embodiments have been shown and described and that all changes, modifications and equivalents that come within the spirit of the disclosures described heretofore and/or defined by the following claims are desired to be protected. In addition, all publications cited herein are indicative of the level of skill in the art and are hereby incorporated by reference in their entirety as if each had been individually incorporated by reference and fully set forth.

What is claimed is:

1. A chemistry matrix composition for use in determining the concentration of an analyte with reduced interference from other constituents present with the analyte, the matrix comprising glucose dehydrogenase, nicotinamide adenine dinucleotide, a 5-alkylphenazine quaternary salt, and a nitrosoaniline, wherein said matrix is stable at a pH of from about 6.5 to about 8.5 and is photochemically stable.

2. The composition of claim 1, wherein the 5-alkylphenazine quaternary salt is a compound having the formula:

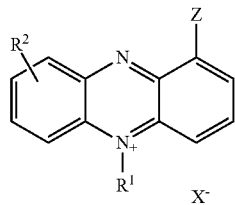

where:

Z is selected from the group consisting of —(CH$_2$)$_m$COOH, —NHAc, and —OY, where m can any integer ranging from 0 to about 6 and Y is selected from the group consisting of

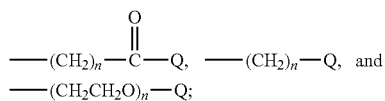

where n is an integer ranging from about 1 to about 4, Q is —OH, —OR$^1$, —NH$_2$, —NHR$^2$, —NR$^2$R$^3$, —NH(CH$_2$)$_o$NR$^2$R$^3$, —NH(CH$_2$)$_o$OH, —NHCH$_2$CH$_2$—(OCH$_2$CH$_2$)$_o$-G, —(CH$_2$)$_o$NR$^2$R$^3$, —OCH$_2$CH$_2$)$_o$NR$^2$R$^3$ or —(OCH$_2$CH$_2$)$_o$OH, where G is —COOH, NR$^2$R$^3$, or

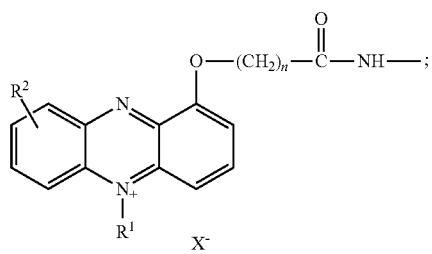

R$^1$ is a C$_1$ to C$_6$ alkyl group, R$^2$ and R$^3$ are the same or different and each represents a H or a C$_1$ to C$_6$ alkyl group, o is an integer ranging from about 1 to about 6; and X is an anion selected from the group consisting of halide, sulfate, alkyl sulfate, phosphate, phosphite, carboxylate, CF$_3$COO$^-$, CH$_3$OSO$_2^-$, C$_2$H$_5$OSO$_2^-$, and CH$_3$SO$_3^-$.

3. The composition of claim 1, wherein the nitrosoaniline is a compound having the formula:

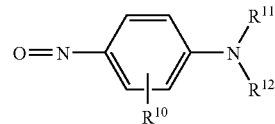

and,

R$^{10}$ denotes hydrogen, halogen, alkoxy or alkylthio,
R$^{11}$ represents an alkyl or a hydroxyalkyl residue and
R$^{12}$ represents a hydroxyalkyl residue or
R$^{11}$ and R$^{12}$ are the same or different and each represents a dialkylaminoalkyl residue, a hydroxyalkyl, a hydroxyalkoxyalkyl or alkoxyalkyl residue, or
R$^{11}$ and R$^{12}$ form an alkylene residue interrupted by sulphur, nitrogen, or a substituted nitrogen residue, or
provided if R$^{10}$ is in the ortho position to NR$^{10}$R$^{11}$, R$^{11}$ also together with R$^{10}$ represents an alkylene residue wherein R$^{12}$ then represents a hydroxyalkyl residue or,
R$^{10}$ and R$^{12}$ are the same or different and each represents a hydroxyalkyl residue or a salt thereof.

4. The chemistry matrix of claim 2, wherein R$^1$ is C$_2$H$_5$.

5. The chemistry matrix of claim 4, wherein said nitrosoaniline has the formula:

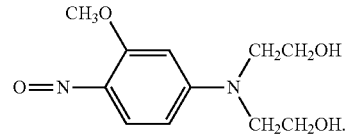

6. The chemistry matrix composition of claim 5, wherein Z is —OY; Y is —(CH$_2$)$_n$COOQ; Q is OH; and n=3.

7. The chemistry matrix composition of claim 5, wherein Z is —OY; Y is —(CH$_2$)$_n$COOQ; Q is —NHCH$_2$CH$_2$—(OCH$_2$CH$_2$)$_o$- G; G is —COOH; and o is 4.

8. The chemistry matrix composition of claim 5, wherein Z is —OY; Y is —(CH$_2$)$_n$Q; Q is —NH$_2$ and n is 4.

9. The chemistry matrix composition of claim 5, wherein Z is —OY; Y is —(CH$_2$)$_n$Q; Q is —OH and n is 3.

10. The chemistry matrix composition of claim 5, wherein Z is —OY; Y is —(CH$_2$)$_n$Q; Q is —OR$^2$; R$^2$ is Me; and n is 4.

11. The chemistry matrix composition of claim 5, wherein Z is —(CH$_2$)$_m$COOH and m is 1.

12. The chemistry matrix composition of claim 5, wherein Z is —NHAc.

13. A chemistry matrix composition for use in analyzing the concentration of an analyte with reduced interference from other constituents present with the analyte, the composition comprising glucose dehydrogenase; nicotinamide adenine dinucleotide; a nitrosoaniline and a 5-alkylphenazine quaternary salt having the formula:

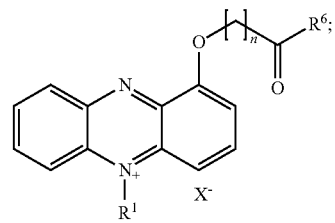

where R⁶ is selected from the group consisting of —OH, —OR¹, —NH₂, —NHR², —NR²R³, —NH(CH₂)ₘNR₂, —NH(CH₂)ₘOH, —O(CH₂)ₘNH₂, and —O(CH₂)ₘOH, R¹ is a C₁ to C₆ alkyl group, R² and R³ are the same or different and each represents a H or a C₁ to C₆ alkyl group, X⁻ is an anion selected from the group consisting of halide, sulfate, alkyl sulfate, phosphate, phosphite, carboxylate, CF₃COO⁻, CH₃OSO₂⁻, C₂H₅OSO₂⁻, and CH₃SO₃⁻, and n and m are integers ranging from about 1 to about 6.

14. The chemistry matrix of claim 13, wherein R¹ is C₂H₅.

15. The chemistry matrix of claim 14, wherein said nitrosoaniline has the formula:

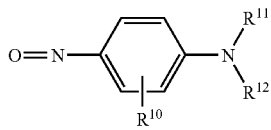

and,

R¹⁰ denotes hydrogen, halogen, alkoxy or alkylthio,

R¹¹ represents an alkyl or a hydroxyalkyl residue and R¹² represents a hydroxyalkyl residue or R¹¹ and R¹² are the same or different and each represents a dialkylaminoalkyl residue, a hydroxyalkyl, a hydroxyalkoxyalkyl or alkoxyalkyl residue, or R¹¹ and R¹² form an alkylene residue interrupted by sulphur, nitrogen, or a substituted nitrogen residue, or provided if R¹⁰ is in the ortho position to NR¹⁰OR¹¹, R¹¹ also together with R¹⁰ represents an alkylene residue wherein R¹² then represents a hydroxyalkyl residue or, R¹⁰ and R¹² are the same or different and each represents a hydroxyalkyl residue or a salt thereof.

16. The chemistry matrix of claim 15, wherein said nitrosoaniline has the formula:

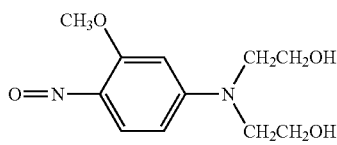

17. A chemistry matrix composition for use in analyzing the concentration of an analyte, comprising glucose dehydrogenase, nicotinamide adenine dinucleotide, a nitrosoaniline precursor and a photochemically stable 1-carboxyalkyloxy-5-alkylphenazine useful for determining the concentration of an analyte.

18. The chemistry matrix of claim 17, wherein the nitrosoaniline has the formula:

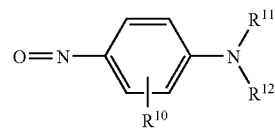

wherein,

R¹⁰ denotes hydrogen, halogen, alkoxy or alkylthio,

R¹¹ represents an alkyl or a hydroxyalkyl residue and R¹² represents a Hydroxyalkyl residue or R¹¹ and R¹² are the same or different and each represents a dialkylaminoalkyl residue, a hydroxyalkyl, a hydroxyalkoxyalkyl or alkoxyalkyl residue, or R¹¹ and R¹² form an alkylene residue interrupted by sulphur, nitrogen, or a substituted nitrogen residue, or provided if R¹⁰ is in the ortho position to NR¹¹R¹², R¹¹ also together with R¹⁰ represents an alkylene residue wherein R¹² then represents a hydroxyalkyl residue.

19. The chemistry matrix of claim 18, wherein the 5-alkyl-1-carboxyalkyloxyphenazine is a compound having the formula:

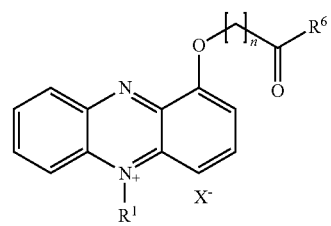

wherein where R⁶ is selected from the group consisting of —OH, —OR¹, —NH₂, —NHR², —NR²R³, —NH(CH₂)ₘNR₂, —NH(CH₂)ₘOH, —O(CH₂)ₘNH₂, and —O(CH₂)ₘOH, R² is a C₁ to C₆ alkyl group, R¹ is C₁ to C₆ alkyl, R² and R³ are the same or different and each represents a H or a C₁ to C₆ alkyl group, X⁻ is an anion selected from the group consisting of halide, sulfate, alkyl sulfate, phosphate, phosphite, carboxylate, CF₃COO⁻, CH₃OSO₂⁻, C₂H₅OSO₂⁻, and CH₃SO₃⁻, and n and m are integers ranging from about 1 to about 6.

20. The chemistry matrix composition of claim 1 for use in an electrochemical process for determining the concentration of an analyte with reduced interference from other constituents present with the analyte.

21. The chemistry matrix composition of claim 20 in which the 5-alkylphenazine quaternary salt is a 5-ethylphenazine salt.

22. The chemistry matrix composition of claim 21 in which the 5-ethylphenazine salt is 1-(3-carboxypropyloxy)-5-ethylphenazine.

* * * * *

UNITED STATES PATENT AND TRADEMARK OFFICE
CERTIFICATE OF CORRECTION

Figure 3:
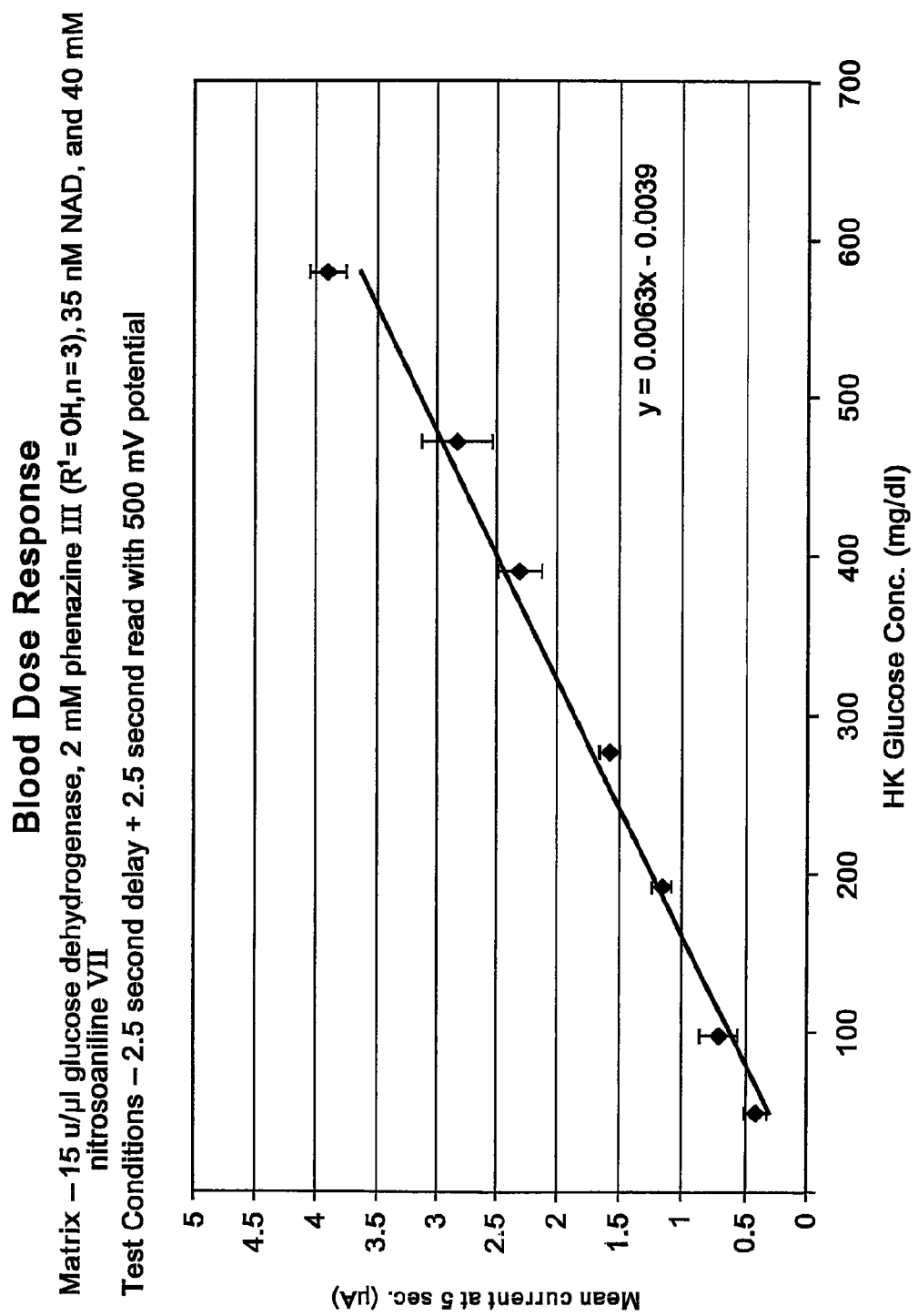
FIG. 3 is a plot illustrating the linear nature of the blood/glucose response determined with the new chemistry matrix described in Example 1.

PATENT NO. : 8,008,037 B2  
APPLICATION NO. : 12/056473  
DATED : August 30, 2011  
INVENTOR(S) : Christopher D. Wilsey It is certified that error appears in the above-identified patent and that said Letters Patent is hereby corrected as shown below:

Fig. 3, sheet 2 of 5, in the title, replace the reference "phenazine III" with --phenazine IIb--

Fig. 3, sheet 2 of 5, in the title, replace the concentration from "35 nM" with --35 mM--

Figure 4:
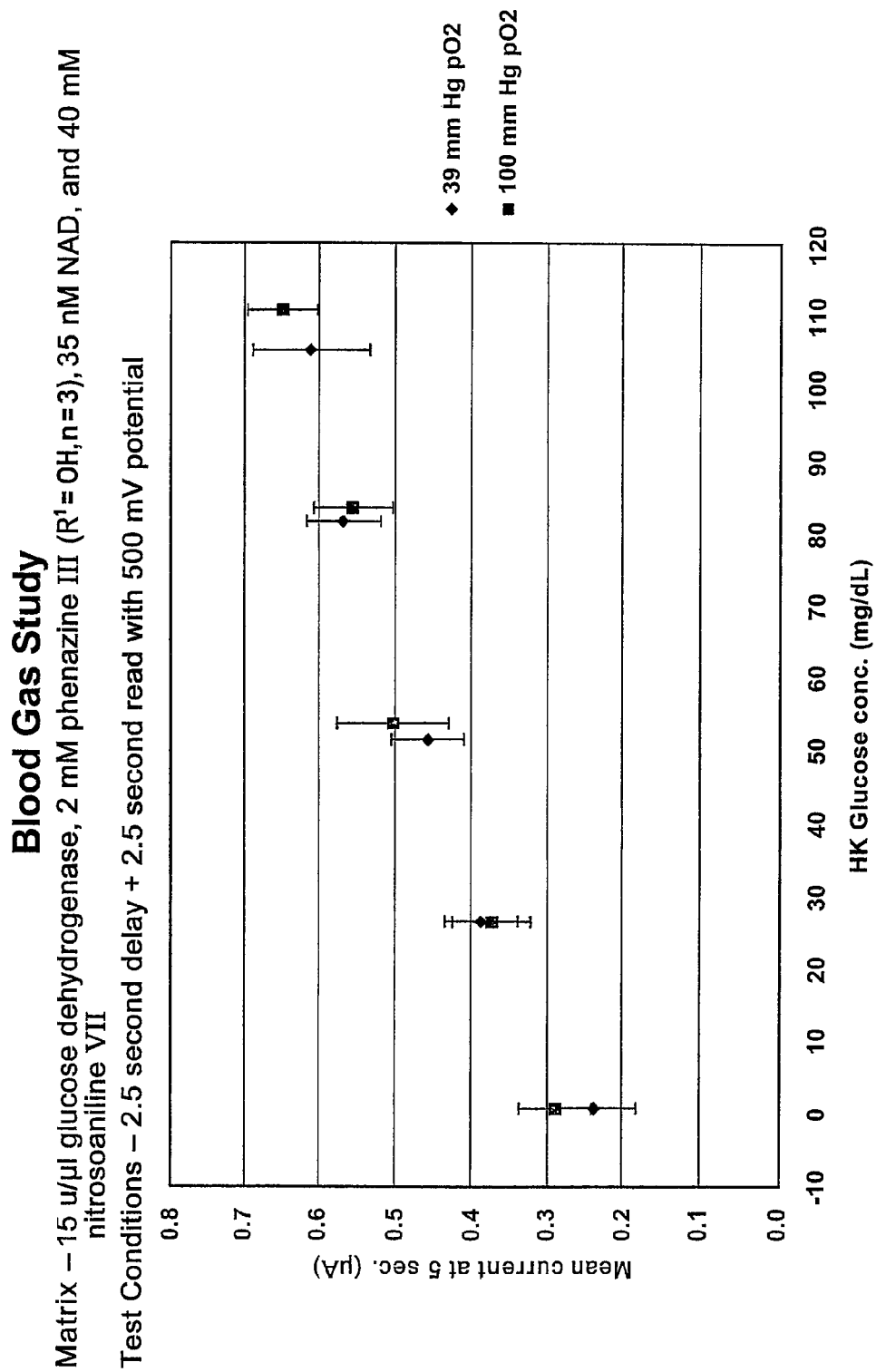
FIG. 4 is a plot illustrating the lack of oxygen interference at two oxygen levels and at glucose levels ranging from about 0 to about 120 mg/dL.

Fig. 4, sheet 3 of 5, in the title, replace the reference "phenazine III" with --phenazine IIb--

Fig. 4, sheet 3 of 5, in the title, replace the concentration from "35 nM" with --35 mM--

Fig. 5, sheet 4 of 5, in the title, replace the reference "phenazine III" with --phenazine IIb--

Fig. 5, sheet 4 of 5, in the title, replace the concentration from "35 nM" with --35 mM--

Fig. 6, sheet 5 of 5, in the title, replace the reference "phenazine III" with --phenazine IIb--

Fig. 6, sheet 5 of 5, in the title, replace the concentration from "35 nM" with --35 mM--

Signed and Sealed this  
Nineteenth Day of March, 2013

Teresa Stanek Rea  
*Acting Director of the United States Patent and Trademark Office*